(12) United States Patent
Akagi et al.

(10) Patent No.: US 9,970,750 B2
(45) Date of Patent: May 15, 2018

(54) SHAPE INSPECTION APPARATUS FOR METALLIC BODY AND SHAPE INSPECTION METHOD FOR METALLIC BODY

(71) Applicant: NIPPON STEEL & SUMITOMO METAL CORPORATION, Tokyo (JP)

(72) Inventors: Toshio Akagi, Tokyo (JP); Yusuke Konno, Tokyo (JP); Hironao Yamaji, Tokyo (JP); Jun Umemura, Tokyo (JP)

(73) Assignee: NIPPON STEEL & SUMITOMO METAL CORPORATION, Tokyo (JP)

( * ) Notice: Subject to any disclaimer, the term of this patent is extended or adjusted under 35 U.S.C. 154(b) by 0 days. days.

(21) Appl. No.: 15/510,827

(22) PCT Filed: May 24, 2016

(86) PCT No.: PCT/JP2016/065261
§ 371 (c)(1),
(2) Date: Mar. 13, 2017

(87) PCT Pub. No.: WO2016/194698
PCT Pub. Date: Dec. 8, 2016

(65) Prior Publication Data
US 2018/0087898 A1   Mar. 29, 2018

(30) Foreign Application Priority Data
May 29, 2015   (JP) .................................. 2015-109680

(51) Int. Cl.
*G01B 11/24* (2006.01)
*G01B 11/25* (2006.01)
(Continued)

(52) U.S. Cl.
CPC ........ *G01B 11/2509* (2013.01); *G01B 11/245* (2013.01); *G01B 11/26* (2013.01);
(Continued)

(58) Field of Classification Search
CPC ....... G01B 11/24; G01B 11/25; G01B 11/306; G01B 11/245; G06T 7/0057
(Continued)

(56) References Cited

U.S. PATENT DOCUMENTS 6,556,706 B1 * 4/2003 Geng ................. G01B 11/2509
382/154
2014/0092288 A1 * 4/2014 Hattery ................ A61B 5/0059
348/302
(Continued)

FOREIGN PATENT DOCUMENTS

CN   102830123 A   12/2012
JP   63-293405 A   11/1988
(Continued)

OTHER PUBLICATIONS

Extended European Search Report for corresponding European Application No. 16803133.4, dated Dec. 15, 2017.
(Continued)

*Primary Examiner* — MD M Rahman
(74) *Attorney, Agent, or Firm* — Birch, Stewart, Kolasch & Birch, LLP

(57) ABSTRACT

[Object] To perform shape inspection of a metallic body in a simple way at higher speed with higher density.
[Solution] An apparatus of the present invention includes: a measurement apparatus configured to irradiate a metallic body with at least two illumination light beams, and measure reflected light separately; and an arithmetic processing apparatus configured to calculate information used for shape inspection of the metallic body on the basis of measurement results. The measurement apparatus includes a plurality of illumination light sources configured to emit strip-shaped illumination light having different peak wavelengths, and a plurality of monochrome line sensor cameras that have band-pass filters and are aligned vertically above a surface of the metallic body and set to capture images of the same portion of the metallic body by their respective shift lenses, the number of the monochrome line sensor cameras being the same as the number of the peak wavelengths of the emitted illumination light. At least two of the plurality of illumination light sources are provided in a manner that an
(Continued)

angle formed by a normal direction to the surface of the metallic body and an optical axis of the first illumination light source is substantially equal to an angle formed by the normal direction and an optical axis of the second illumination light source and the two illumination light sources face each other with the line sensor cameras therebetween in a relative movement direction of the metallic body and the measurement apparatus.

16 Claims, 20 Drawing Sheets

(51) Int. Cl.
*G01B 11/245* (2006.01)
*G01B 11/26* (2006.01)
*G01N 21/892* (2006.01)
*G01N 21/86* (2006.01)
*G01N 21/89* (2006.01)

(52) U.S. Cl.
CPC ... *G01N 21/892* (2013.01); *G01N 2021/8636* (2013.01); *G01N 2021/8918* (2013.01)

(58) Field of Classification Search
USPC .......................................... 356/601
See application file for complete search history.

(56) References Cited

U.S. PATENT DOCUMENTS

| | | | |
|---|---|---|---|
| 2014/0118502 A1 | 5/2014 | Jang | |
| 2015/0015692 A1* | 1/2015 | Smart | G01J 3/2823 348/77 |

FOREIGN PATENT DOCUMENTS

| | | |
|---|---|---|
| JP | 2003-269931 A | 9/2003 |
| JP | 2004-3930 A | 1/2004 |
| JP | 2004-132801 A | 4/2004 |
| JP | 11-63954 A | 8/2007 |
| JP | 2007-201038 A | 8/2007 |
| JP | 4525090 B2 | 8/2010 |
| JP | 2012-225795 A | 11/2012 |
| WO | WO 2010/02424 A | 3/2010 |

OTHER PUBLICATIONS

He, "Trilinear Cameras Offer High-Speed Color Imaging Solutions," Photonics Spectra, May 5, 2013, 6 pages.
Kang et al., "Development of an Inspection System for Planar Steel Surface Using Multispectral Photometric Stereo," Optical Engineering, vol. 52, No. 3, Mar. 2013, pp. 039701-1-039701-7 (8 pages total).
Landström et al., "Sub-Millimeter Crack Detection in Casted Steel Using Color Photometric Stereo," 2013 International Conference on Digital Image Computing: Techniques and Applications (DICTA), Nov. 26, 2013, 7 pages.
International Search Report for PCT/JP2016/065261 dated on Aug. 16, 2016.
Tomita et al., "A Method for Shape Reconstruction of Solid Objects based on Color Photometric Stereo", IPSJ SIG Notes Computer Vision and Image Media (CVIM), vol. 1992, No. 90, Information Processing Society of Japan, Nov. 19, 1992, pp. 115-120.
Written Opinion of the International Searching Authority for PCT/JP2016/065261 (PCT/ISA/237) dated Aug. 16, 2016.

* cited by examiner

V GROOVE

FIG. 16
| IMAGE WITH SINGLE COLOR | |
|---|---|
| B IMAGE (460 nm) | 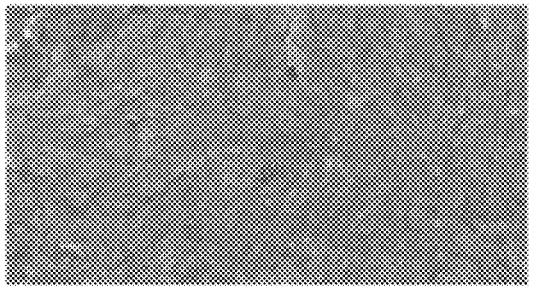 |
| G IMAGE (530 nm) | 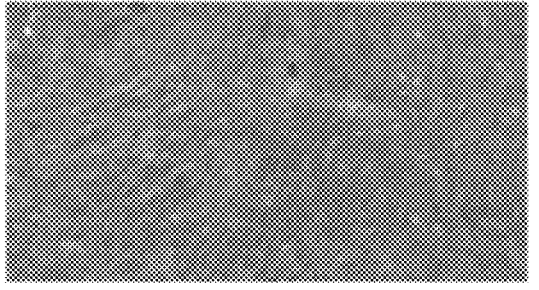 |
| R IMAGE (640 nm) |  | ively equal to a second angle formed by the normal
SHAPE INSPECTION APPARATUS FOR METALLIC BODY AND SHAPE INSPECTION METHOD FOR METALLIC BODY

TECHNICAL FIELD

The present invention relates to a shape inspection apparatus for a metallic body and a shape inspection method for a metallic body.

BACKGROUND ART

One of methods for measuring the surface shape of a measurement object is to use illumination light utilizing a fluorescent lamp, a light-emitting diode (LED), a laser beam, or the like, and capture an image of reflected light from the measurement object of the illumination light to measure the surface shape of the measurement object.

For example, Patent Literature 1 below discloses a method of measuring the shape of a tire surface by a so-called light-section method by using linear light and an image capturing camera.

In addition, Patent Literature 2 below discloses a technology of using a periodically-modulated linear laser beam as illumination light and capturing an image of reflected light of this linear laser beam by a delay-integration-type image capturing device, and thus measuring the shape of a measurement object according to a stripe image obtained.

CITATION LIST

Patent Literature

Patent Literature 1: JP 2012-225795A
Patent Literature 2: JP 2004-3930A
Patent Literature 3: Chinese Patent Application Publication No. 102830123

SUMMARY OF INVENTION

Technical Problem

However, in the light-section method as disclosed in Patent Literature 1, only one cross-sectional shape can be obtained from one captured image, which makes it difficult to measure the whole shape of the measurement object at high speed.

Moreover, in the method using a delay-integration-type image capturing device as disclosed in Patent Literature 2, only one cross-sectional shape can be obtained from each stripe constituting the stripe image, which makes high-density shape measurement difficult.

Hence, the present inventors carried out extensive studies on a method by which the shape of a metallic body can be inspected at higher speed with higher density. The studies by the present inventors included examination of applying, to shape measurement of a metallic body, an inspection method of irradiating the surface of a metallic body (e.g., a steel plate) with red light and blue light and capturing an image of reflected light from the metallic body with a color line camera, thereby inspecting fine defects on the surface of the metallic body, as disclosed in Patent Literature 3, though this technology is not related to shape inspection of a metallic body.

However, in an ordinary color line sensor camera like that used in Patent Literature 3, wavelength bands of light that can be received by the camera are limited to three colors of R, G and B, and thus wavelengths of illumination light cannot be selected arbitrarily. It is possible to newly design a color filter for a color line sensor camera in order to select wavelengths of illumination light arbitrarily, but cost for newly creating a color filter would be needed in such a case. Furthermore, the method used in Patent Literature 3 has a problem of low flexibility against disturbance when a change in color occurs in a steel plate in a production process. In addition, the color line sensor camera used in Patent Literature 3 has a problem in that it has lower speed than a monochrome line sensor camera, which makes it difficult to increase the speed of a shape inspection process for a metallic body.

Hence, the present invention is made in view of the above problem, and an object of the present invention is to provide a shape inspection apparatus for a metallic body and a shape inspection method for a metallic body that are capable of performing shape inspection of a metallic body in a simple way at higher speed with higher density.

Solution to Problem

According to an aspect of the present invention in order to achieve the above-mentioned object, there is provided a shape inspection apparatus for a metallic body, including: a measurement apparatus configured to irradiate a metallic body with at least two illumination light beams, and measure reflected light of the at least two illumination light beams from a same portion of the metallic body separately; and an arithmetic processing apparatus configured to calculate information used for shape inspection of the metallic body on the basis of measurement results of luminance values of the reflected light obtained by the measurement apparatus, while controlling a measurement process by the measurement apparatus. The measurement apparatus includes a plurality of illumination light sources configured to irradiate the metallic body with strip-shaped illumination light having mutually different peak wavelengths, and a line sensor camera group composed of a plurality of monochrome line sensor cameras that are aligned vertically above a surface of the metallic body and set to capture images of the same portion of the metallic body by their respective shift lenses, the number of the monochrome line sensor cameras being the same as the number of the peak wavelengths of the illumination light emitted from the plurality of illumination light sources. At least two of the plurality of illumination light sources are provided in a manner that a first angle formed by a normal direction to the surface of the metallic body and an optical axis of the first illumination light source is substantially equal to a second angle formed by the normal direction and an optical axis of the second illumination light source and the two illumination light sources face each other with the monochrome line sensor cameras therebetween in a relative movement direction of the metallic body and the measurement apparatus. The monochrome line sensor cameras are provided with band-pass filters having transmitted wavelength bands corresponding to peak wavelengths of different illumination light sources among the plurality of illumination light sources, each band-pass filter being provided to precede an image sensor of the corresponding monochrome line sensor camera, and reflected light of illumination light from the illumination light source having a peak wavelength included in the transmitted wavelength band of the band-pass filter forms an image in each monochrome line sensor camera. The arithmetic processing apparatus calculates an inclination of the surface of the metallic body as the information by using a difference between a luminance value of the monochrome line sensor camera having the band-pass filter that transmits a peak wavelength of the first illumination light source with the highest transmittance and a luminance value of the monochrome line sensor camera having the band-pass filter that transmits a peak wavelength of the second illumination light source with the highest transmittance.

An illumination light source group composed of a plurality of illumination light sources configured to emit illumination light that forms images in the respective monochrome line sensor cameras of the line sensor camera group may be provided at each of an upstream side and a downstream side along the relative movement direction with respect to the line sensor camera group.

The first angle and the second angle are each preferably 30 degrees or more.

The measurement apparatus may include three or more illumination light sources, and the arithmetic processing apparatus may decide beforehand a combination of peak wavelengths of the illumination light that provides the reflected light used in calculating the difference on the basis of a reflection spectrum of the metallic body.

The measurement apparatus may include three or more illumination light sources, each illumination light source being arranged in a manner that a longitudinal direction of the illumination light source is substantially parallel to a width direction of the metallic body, and the arithmetic processing apparatus may dynamically decide a combination of peak wavelengths of the illumination light that provides the reflected light used in calculating the difference in a manner that the combination makes an in-plane average value of the calculated differences closest to zero.

The arithmetic processing apparatus preferably specifies a direction of the inclination on the basis of a sign of the difference and specifies a magnitude of the inclination on the basis of an absolute value of the difference.

The arithmetic processing apparatus may further calculate a height of the surface of the metallic body as the information by integrating the calculated inclination of the surface of the metallic body along a relative movement direction of the monochrome line sensor cameras and the metallic body.

The arithmetic processing apparatus may inspect a shape of the metallic body by comparing the calculated inclination of the surface of the metallic body with a predetermined threshold value.

According to another aspect of the present invention in order to achieve the above-mentioned object, there is provided a shape inspection method for a metallic body, including: irradiating a metallic body with at least two illumination light beams, and measuring reflected light of the illumination light beams from the metallic body separately, by a measurement apparatus including a plurality of illumination light sources configured to irradiate the metallic body with strip-shaped illumination light having mutually different peak wavelengths, and a line sensor camera group composed of a plurality of monochrome line sensor cameras that are aligned vertically above a surface of the metallic body and set to capture images of a same portion of the metallic body by their respective shift lenses, the number of the monochrome line sensor cameras being the same as the number of the peak wavelengths of the illumination light emitted from the plurality of illumination light sources, in which at least two of the plurality of illumination light sources are provided in a manner that a first angle formed by a normal direction to the surface of the metallic body and an optical axis of the first illumination light source is substantially equal to a second angle formed by the normal direction and an optical axis of the second illumination light source and the two illumination light sources face each other with the monochrome line sensor cameras therebetween in a relative movement direction of the metallic body and the measurement apparatus, and the monochrome line sensor cameras are provided with band-pass filters having transmitted wavelength bands corresponding to peak wavelengths of different illumination light sources among the plurality of illumination light sources, each band-pass filter being provided to precede an image sensor of the corresponding monochrome line sensor camera, and reflected light of illumination light from the illumination light source having a peak wavelength included in the transmitted wavelength band of the band-pass filter forms an image in each monochrome line sensor camera; and calculating, by an arithmetic processing apparatus configured to calculate information for shape inspection of the metallic body on the basis of measurement results of luminance values of the reflected light obtained by the measurement apparatus, while controlling a measurement process by the measurement apparatus, an inclination of the surface of the metallic body as the information by using a difference between a luminance value of the monochrome line sensor camera having the band-pass filter that transmits a peak wavelength of the first illumination light source with the highest transmittance and a luminance value of the monochrome line sensor camera having the band-pass filter that transmits a peak wavelength of the second illumination light source with the highest transmittance.

An illumination light source group composed of a plurality of illumination light sources configured to emit illumination light that forms images in the respective monochrome line sensor cameras of the line sensor camera group may be provided at each of an upstream side and a downstream side along the relative movement direction with respect to the line sensor camera group.

The first angle and the second angle are each preferably set to 30 degrees or more.

The measurement apparatus may include three or more illumination light sources, and the arithmetic processing apparatus may decide beforehand a combination of peak wavelengths of the illumination light that provides the reflected light used in calculating the difference on the basis of a reflection spectrum of the metallic body.

The measurement apparatus may include three or more illumination light sources, each illumination light source being arranged in a manner that a longitudinal direction of the illumination light source is substantially parallel to a width direction of the metallic body, and the arithmetic processing apparatus may dynamically decide a combination of peak wavelengths of the illumination light that provides the reflected light used in calculating the difference in a manner that the combination makes an in-plane average value of the calculated differences closest to zero.

The arithmetic processing apparatus preferably specifies a direction of the inclination on the basis of a sign of the difference and specifies a magnitude of the inclination on the basis of an absolute value of the difference.

In the shape inspection method for a metallic body, the arithmetic processing apparatus may further calculate a height of the surface of the metallic body as the information by integrating the calculated inclination of the surface of the metallic body along a relative movement direction of the monochrome line sensor cameras and the metallic body.

In the shape inspection method for a metallic body, the arithmetic processing apparatus may inspect a shape of the metallic body by comparing the calculated inclination of the surface of the metallic body with a predetermined threshold value.

Advantageous Effects of Invention

According to the present invention, shape inspection of a metallic body can be performed in a simple way at higher speed with higher density.

BRIEF DESCRIPTION OF DRAWINGS

FIG. 16 is an explanatory diagram for explaining Example 2.

DESCRIPTION OF EMBODIMENTS

Hereinafter, (a) preferred embodiment(s) of the present invention will be described in detail with reference to the appended drawings. In this specification and the drawings, elements that have substantially the same function and structure are denoted with the same reference signs, and repeated explanation is omitted.

(Configuration of Shape Inspection Apparatus)

Figure 1:
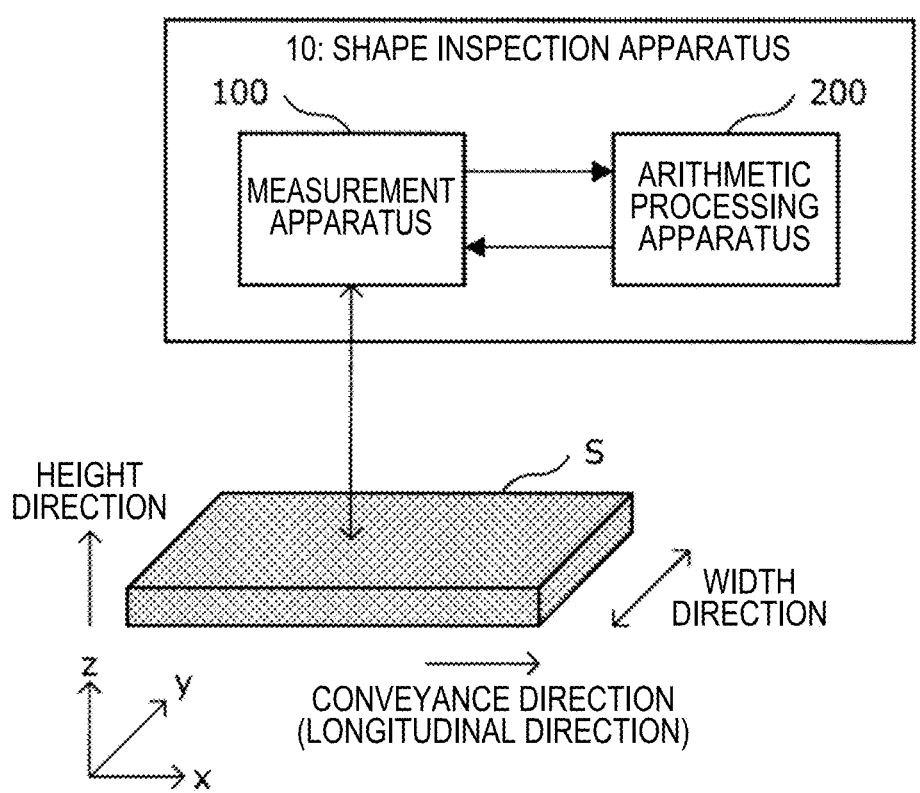
FIG. 1 is an explanatory diagram schematically illustrating an example of a shape inspection apparatus according to an embodiment of the present invention.

First, an overall configuration of a shape inspection apparatus for a metallic body (hereinafter, also simply called a "shape inspection apparatus") 10 according to an embodiment of the present invention will be described with reference to FIG. 1. FIG. 1 is an explanatory diagram illustrating a configuration example of the shape inspection apparatus 10 according to the present embodiment.

The shape inspection apparatus 10 according to the present embodiment is an apparatus that inspects the shapes (e.g., surface shapes) of various metallic bodies S, such as a steel plate placed at a predetermined location and a steel plate conveyed on a predetermined conveyor line.

Here, the shape inspection apparatus 10 and the metallic body move relative to each other; as described above, the shape inspection apparatus 10 may be configured in a manner that a measurement apparatus 100 of the shape inspection apparatus 10 is fixed with respect to the conveyor line and the metallic body is conveyed on the conveyor line, or in a manner that the measurement apparatus 100 moves with respect to a still metallic body.

A macroscopic shape of the metallic body S is not particularly limited and may be, for example, a plate shape (e.g., a slab or a billet) or a strip shape.

Components of the metallic body S are also not particularly limited, and the metallic body S may be various types of steel containing an iron element as the main component, various types of alloy of iron and other metal elements, or various types of nonferrous metal.

In the following description, the metallic body S is assumed to be conveyed along the longitudinal direction of the metallic body S on a conveyor line (not illustrated), and the longitudinal direction of the metallic body S is also called a conveyance direction.

This shape inspection apparatus 10 mainly includes the measurement apparatus 100 and an arithmetic processing apparatus 200, as illustrated in FIG. 1.

Under control of the arithmetic processing apparatus 200, the measurement apparatus 100 irradiates the metallic body S (specifically, the surface of the metallic body S) with at least two types of illumination light, and measures reflected light from the metallic body S (specifically, the surface of the metallic body S) of the illumination light separately to generate data on luminance values of the reflected light. The measurement apparatus 100 outputs the generated data on the luminance values of the reflected light to the arithmetic processing apparatus 200.

The arithmetic processing apparatus 200 controls a measurement process of the metallic body S by the measurement apparatus 100. In addition, the arithmetic processing apparatus 200 acquires the data on the luminance values of the reflected light, generated by the measurement apparatus 100, and performs data processing, which will be described in detail later, on the acquired data on the luminance values, thereby calculating various types of information used for inspecting the shape (specifically, surface shape) of the metallic body S. In the following description, various types of information used for shape inspection is collectively called "information for inspection". Examples of the information for inspection calculated by the arithmetic processing apparatus 200 include, as will be described in detail later, information on an inclination of the surface of the metallic body S, which is calculated on the basis of a difference between luminance values of reflected light of two types of illumination light, and information on a height of the surface of the metallic body S, which is obtained by integrating the inclination of the surface. In other words, the information on an inclination of the surface of the metallic body S and the information on a height of the surface serve as information indicating the shape of the metallic body S.

The measurement process of the metallic body S by the measurement apparatus 100 and a calculation process of information for inspection by the arithmetic processing apparatus 200 can be performed in real time along with conveyance of the metallic body S. A user of the shape inspection apparatus 10 can recognize in real time the shape of the metallic body S and inspect the metallic body S by focusing on inspection results output from the shape inspection apparatus 10 (specifically, the arithmetic processing apparatus 200).

Hereinafter, each of the measurement apparatus 100 and the arithmetic processing apparatus 200 will be described in detail.

<Measurement Apparatus 100>

First, the measurement apparatus 100 according to the present embodiment will be described in detail with reference to FIGS. 2A to 4.

Figure 3:
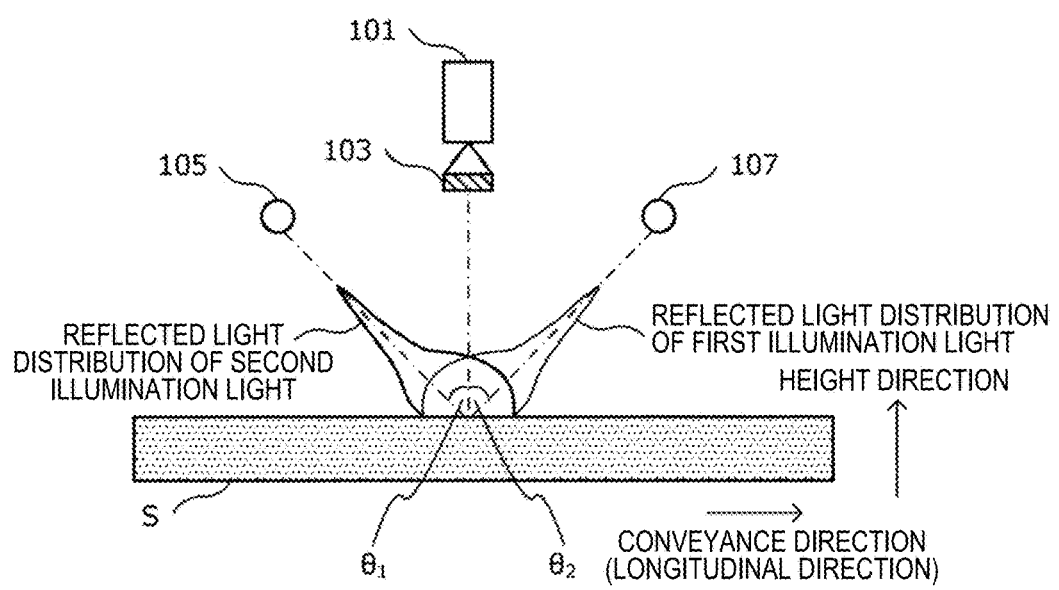
FIG. 3 is an explanatory diagram for explaining a measurement apparatus according to the embodiment.
Figure 4:
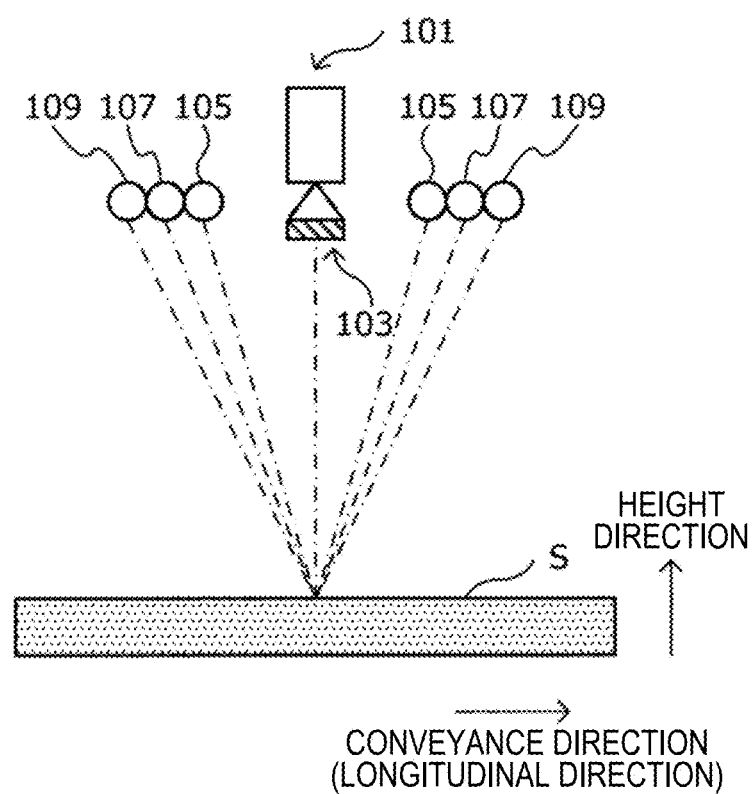
FIG. 4 is an explanatory diagram schematically illustrating another example of a measurement apparatus included in a shape inspection apparatus according to the embodiment.

FIGS. 2A to 2D are explanatory diagrams schematically illustrating an example of a measurement apparatus included in a shape inspection apparatus according to the present embodiment. FIG. 3 is an explanatory diagram for explaining a measurement apparatus according to the present embodiment. FIG. 4 is an explanatory diagram schematically illustrating another example of a measurement apparatus included in a shape inspection apparatus according to the present embodiment.

Figure 2A:
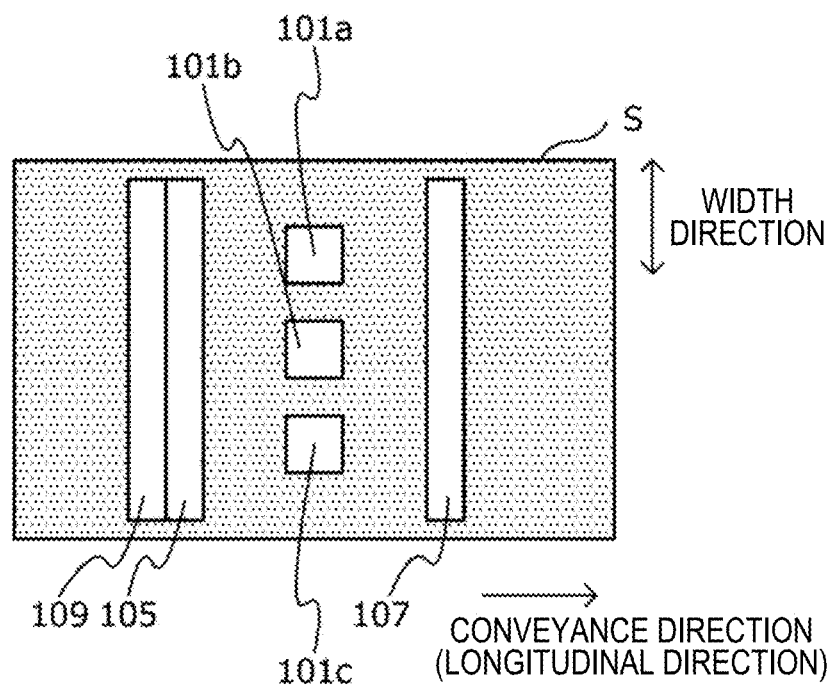
FIG. 2A is an explanatory diagram schematically illustrating an example of a measurement apparatus included in a shape inspection apparatus according to the embodiment.
Figure 2B:
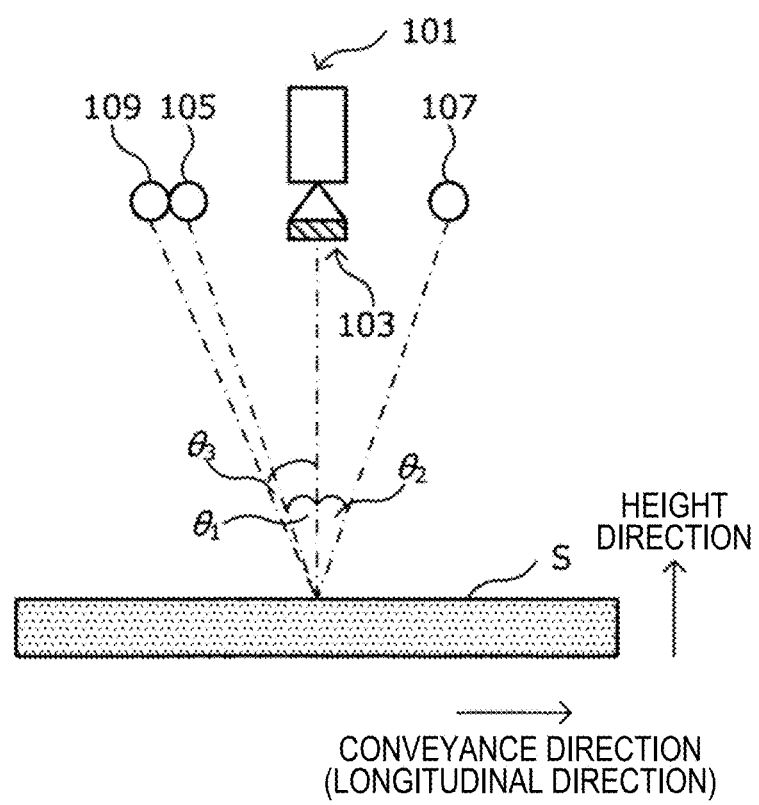
FIG. 2B is an explanatory diagram schematically illustrating an example of a measurement apparatus included in a shape inspection apparatus according to the embodiment.
Figure 2C:
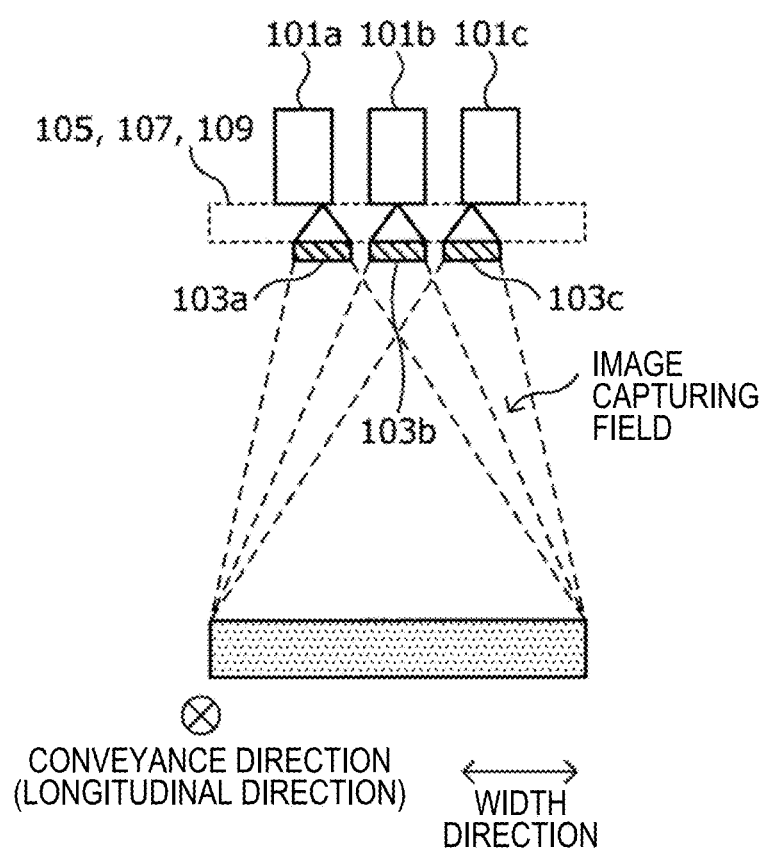
FIG. 2C is an explanatory diagram schematically illustrating an example of a measurement apparatus included in a shape inspection apparatus according to the embodiment.
Figure 2D:
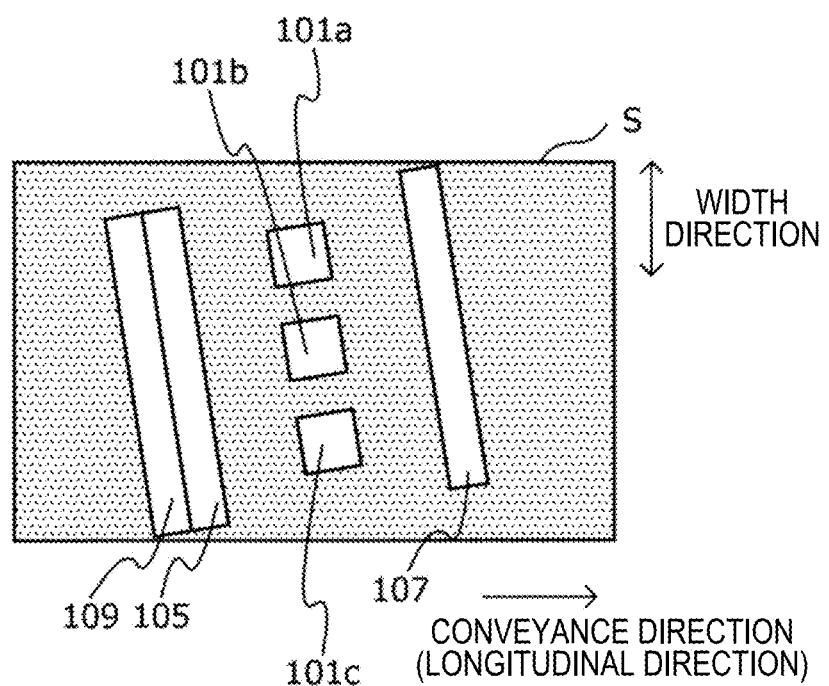
FIG. 2D is an explanatory diagram schematically illustrating an example of a measurement apparatus included in a shape inspection apparatus according to the embodiment.

FIG. 2A is a schematic diagram viewing the measurement apparatus 100 from above the metallic body S. FIG. 2B is a schematic diagram viewing the measurement apparatus 100 from the side along the width direction of the metallic body S. FIG. 2C is a schematic diagram viewing the measurement apparatus 100 from the side along the longitudinal direction of the metallic body S. FIG. 2D is a schematic diagram viewing the measurement apparatus 100 from above the metallic body S.

As illustrated in FIGS. 2A to 2C, the measurement apparatus 100 according to the present embodiment includes at least a line sensor camera group composed of a plurality of monochrome line cameras, and a plurality of illumination light sources that irradiate the metallic body S with strip-shaped illumination light having mutually different peak wavelengths. The line sensor camera group and the plurality of illumination light sources are fixed by known means so that their set positions do not change.

FIGS. 2A to 2C illustrate a case where three illumination light sources that emit three types of illumination light having mutually different peak wavelengths are provided as illumination light sources, but the number of illumination light sources is not limited to the illustrated case. The number of illumination light sources provided in the measurement apparatus 100 according to the present embodiment may be two or four or more. Moreover, the emission spectrum distribution of these light sources may include an overlap as long as peak wavelengths are different from each other.

As illustrated in FIGS. 2B and 2C, a line sensor camera group 101 composed of a plurality of monochrome line sensor cameras has alignment along the longitudinal direction of strip-shaped illumination light (the width direction of the metallic body S in FIG. 2A), vertically above the surface of the metallic body S (the positive direction side of the z-axis). In other words, the line sensor camera group 101 is provided in a manner that a projection axis obtained by projecting the optical axis of each monochrome line sensor camera in the width direction of the metallic body S is perpendicular to the surface of the metallic body S (hereinafter, also called a "metallic body surface") (specifically, in a manner that the projection axis and the tangent plane of the metallic body S at the intersection point of the projection axis and the metallic body surface form a perpendicular angle).

Each monochrome line sensor camera included in the line sensor camera group 101 is equipped with a lens having a shift function (so-called shift lens). The line sensor camera group 101 is set to capture images of the same portion of the surface of the metallic body S, as schematically illustrated in FIG. 2C, by appropriately using the shift function of the shift lenses.

Furthermore, the monochrome line sensor cameras included in the line sensor camera group 101 are provided with band-pass filters 103 having transmitted wavelength bands corresponding to peak wavelengths of different illumination light sources among the plurality of illumination light sources, each band-pass filter 103 being provided to precede an image sensor (not illustrated) of the corresponding monochrome line sensor camera. Here, "corresponding to a peak wavelength of an illumination light source" means that the peak wavelength of the corresponding illumination light source has higher transmittance than the peak wavelengths of other illumination light sources. The band-pass filter 103 is mounted to precede the shift lens in FIGS. 2B and 2C, but the position where the band-pass filter 103 is provided is not limited to the illustrated position, and it may be provided to precede an image sensor inside the monochrome line sensor camera.

Since band-pass filters $103a$, $103b$, and $103c$ described above are mounted, reflected light at the metallic body S of different ones of a plurality of illumination light beams emitted from the plurality of illumination light sources forms images with maximum luminance values in monochrome line sensor cameras $101a$, $101b$, and $101c$. Therefore, the line sensor camera group 101 according to the present embodiment can measure reflected light at the metallic body S of illumination light having mutually different peak wavelengths, which is emitted from illumination light sources described below, separately. Moreover, using this line sensor camera group 101 enables multi-spectral observation of illumination light with N types (N is an integer of 2 or more; three types in FIGS. 2A to 2C) of peak wavelengths in the measurement apparatus 100 according to the present embodiment.

The monochrome line sensor cameras included in the line sensor camera group 101 measure luminance values of reflected light of illumination light corresponding to the band-pass filters 103 separately, generate data corresponding to the obtained measurement results (data on luminance values of reflected light), and output the data to the arithmetic processing apparatus 200 described later.

As such monochrome line sensor cameras, known monochrome line sensor cameras can be used. In general, a monochrome line sensor camera can perform image capturing at higher speed than a color line sensor camera used in Patent Literature 1. Assuming that a color line sensor camera can capture an image of three types of colored light, for example, and the same output interface is used, a three-fold increase in speed can be achieved, as compared with the color line sensor camera, by using three monochrome line sensor cameras as in the present embodiment.

The measurement apparatus 100 according to the present embodiment is provided with three types of illumination light sources of a first illumination light source 105, a second illumination light source 107, and a third illumination light source 109, for example, as the plurality of illumination light sources. The first illumination light source 105 irradiates the surface of the metallic body S with first illumination light, the second illumination light source 107 irradiates the surface of the metallic body S with second illumination light, and the third illumination light source 109 irradiates the surface of the metallic body S with third illumination light. The first illumination light, the second illumination light, and the third illumination light have mutually different peak wavelengths.

Peak wavelengths of illumination light emitted from the respective illumination light sources may be any wavelengths different from each other. In the case where three illumination light sources of the first illumination light source 105, the second illumination light source 107, and the third illumination light source 109 are used as illustrated in FIGS. 2A to 2C, colors of illumination light emitted from the illumination light sources may be selected from red light, green light, and blue light in a manner that an overlap is avoided.

Here, red light indicates visible light with a peak wavelength of 600 to 700 nm, for example, green light indicates visible light with a peak wavelength of 500 to 560 nm, for example, and blue light indicates light with a peak wavelength of 430 nm to 500 nm, for example.

For the sake of convenience, assume that illumination light emitted from the first illumination light source 105 is red light, illumination light emitted from the second illumination light source 107 is green light, and illumination light emitted from the third illumination light source 109 is blue light. Also assume that the band-pass filter 103a of the monochrome line sensor camera 101a has a transmitted wavelength band corresponding to red light, the band-pass filter 103b of the monochrome line sensor camera 101b has a transmitted wavelength band corresponding to green light, and the band-pass filter 103c of the monochrome line sensor camera 101c has a transmitted wavelength corresponding to blue light. In such a case, reflected light at the metallic body S of the first illumination light (red light) emitted from the first illumination light source 105 forms an image with the highest luminance value in the monochrome line sensor camera 101a, reflected light at the metallic body S of the second illumination light (green light) emitted from the second illumination light source 107 forms an image with the highest luminance value in the monochrome line sensor camera 101b, and reflected light at the metallic body S of the third illumination light (blue light) emitted from the third illumination light source 109 forms an image with the highest luminance value in the monochrome line sensor camera 101c.

As illustrated in FIG. 2B, an angle formed by a normal direction to the surface of the metallic body S (specifically, a direction of a projection axis obtained by projecting the optical axis of a monochrome line sensor in the width direction of the metallic body S) and the optical axis of the first illumination light source 105 is denoted by $\theta_1$, an angle formed by the normal direction and the optical axis of the second illumination light source 107 is denoted by $\theta_2$, and an angle formed by the normal direction and the optical axis of the third illumination light source 109 is denoted by $\theta_3$. In this case, in the measurement apparatus 100 according to the present embodiment, at least two illumination light sources are provided above the metallic body S in a manner that the angles specified above are substantially equal. FIG. 2B illustrates a case where the first illumination light source 105 and the second illumination light source 107 are provided in a manner that $\theta_1$ and $\theta_2$ are substantially equal to each other. Moreover, the angles $\theta_1$ and $\theta_3$ in FIG. 2B are preferably as close to each other as possible in magnitude.

Here, "$\theta_1$ and $\theta_2$ are substantially equal to each other" includes not only a case where $\theta_1$ and $\theta_2$ are equal to each other but also a case where $\theta_1$ and $\theta_2$ have an angle difference in a range such that, when images of a plane without unevenness are captured using the first illumination light source 105 and the second illumination light source 107, the plane without unevenness appears the same, with a change in luminance due to soil etc. on the plane taken into account. This angle difference $|\theta_1-\theta_2|$ between $\theta_1$ and $\theta_2$ is preferably 10 degrees or less, for example, further preferably 5 degrees or less. An angle difference in such a range allows two captured images to appear the same when images of a plane without unevenness are captured using the respective illumination light beams.

Here, as the first to third illumination light sources 105 to 109, any light source can be used as long as it can irradiate substantially the entire area of the metallic body S in the width direction with illumination light. As this light source, a rod-like LED light can be utilized, and a laser beam expanded by a rod lens or the like into a linear shape can be used as well, for example. Moreover, as a visible-light light source used as the first to third illumination light sources 105 to 109, a light source like a single-wavelength laser beam or an LED with a narrow emission wavelength band may be used, or a light source that emits light that can be regarded as quasi-monochromatic light by using a light source with a continuous spectrum like a xenon lamp in combination with a color filter may be used.

The first illumination light source 105 and the second illumination light source 107 are provided in a balanced way at the upstream side and the downstream side in the conveyance direction with respect to the line sensor camera group 101, and the third illumination light source 109 is provided at the same side as the first illumination light source 105 in FIG. 2B, but the third illumination light source 109 may be provided at the same side as the second illumination light source 107.

Moreover, the first to third illumination light sources 105 to 109 are installed in a manner that their longitudinal directions are substantially parallel to the width direction of the metallic body S in the example illustrated in FIGS. 2A to 2C, but as illustrated in FIG. 2D, the first to third illumination light sources 105 to 109 may be arranged with inclination in a manner that their longitudinal directions are inclined with respect to the width direction of the metallic body S. The reason for this will be described later.

FIG. 3 illustrates the first illumination light source 105 and the second illumination light source 107 provided in a manner that the optical axes of the illumination light sources form substantially equal angles with the normal direction, extracted from among the three illumination light sources illustrated in FIG. 2B. Since the line sensor camera group 101, the first illumination light source 105, and the second illumination light source 107 are provided as illustrated in FIG. 2B and FIG. 3, when a plane without unevenness is measured, reflected light of the first illumination light has a luminance value substantially equal to a luminance value of reflected light of the second illumination light. On the other hand, when the metallic body surface has unevenness, the unevenness causes a change in the inclination of the surface, causing a difference in reflected light intensity of the first and second illumination light in the camera direction; thus, a difference in luminance value occurs between reflected light of the first illumination light and reflected light of the second illumination light.

In the case where the inclination of the surface due to the unevenness is an inclination parallel to the conveyance direction (more accurately, an inclination rotated around an axis parallel to the conveyance direction), the unevenness cannot be detected with the arrangement of FIG. 2A because reflected light intensity of the first and second illumination light in the camera direction changes similarly. However, by arranging the first to third illumination light sources 105 to 109 diagonally with respect to the conveyance direction as illustrated in FIG. 2D, an inclination parallel to the conveyance direction can be detected on the basis of a difference in luminance value between two reflected light beams.

Also in the case where a luminance value of reflected light of the third illumination light is compared with a luminance value of reflected light of the second illumination light, by providing the first illumination light source 105 and the third illumination light source 109 as close to each other as possible, when a plane without unevenness is measured, reflected light of the third illumination light has a luminance value substantially equal to a luminance value of reflected light of the second illumination light. On the other hand, when the metallic body surface has unevenness, the unevenness causes a difference in luminance value between reflected light of the third illumination light and reflected light of the second illumination light.

The angles $\theta_1$ to $\theta_3$ illustrated in FIG. 2B are preferably as large as possible, as long as there is no constraint on light source installation. Thus, irregular reflection of respective illumination light beams can be measured by the line sensor camera group 101. For example, $\theta_1$ to $\theta_3$ are each preferably 30 degrees or more. By setting each of $\theta_1$ to $\theta_3$ to 30 degrees or more, a change in luminance value relative to an angle change, measured by the line sensor camera group 101, can be further increased.

As will be described in detail later, in the arithmetic processing apparatus 200 according to the present embodiment, luminance values of two reflected light beams, among luminance values of reflected light of a plurality of illumination light beams with which the metallic body S is irradiated, are used, and arithmetic processing using a difference between the selected two luminance values is performed. On this occasion, when the illumination light sources are arranged asymmetrically between the upstream side and the downstream side in the conveyance direction (e.g., the first illumination light source 105 and the third illumination light source 109 are arranged at the upstream side in the conveyance direction, and the second illumination light source 107 is arranged at the downstream side in the conveyance direction) as illustrated in FIGS. 2A to 2C, selection combinations of two reflected light beams are limited. That is, in the example illustrated in FIGS. 2A to 2D, the combinations are limited to two combinations of a combination of reflected light of the first illumination light and reflected light of the second illumination light and a combination of reflected light of the third illumination light and reflected light of the second illumination light.

Hence, in the measurement apparatus 100 according to the present embodiment, an illumination light source group composed of a plurality of illumination light sources that emit illumination light that forms images in the respective monochrome line sensor cameras of the line sensor camera group 101 may be provided at each of the upstream side and the downstream side along the conveyance direction with respect to the line sensor camera group 101. That is, as schematically illustrated in FIG. 4, illumination light source groups each composed of the first to third illumination light sources 105 to 109 that emit the first to third illumination light may be provided symmetrically with respect to the line sensor camera group 101. Providing the illumination light source groups as illustrated in FIG. 4 improves the flexibility in combining reflected light beams used for arithmetic processing, allowing all combinations of illumination light beams.

The measurement apparatus 100 according to the present embodiment has been described in detail with reference to FIGS. 2A to 4.

<Arithmetic Processing Apparatus 200>

Figure 5:
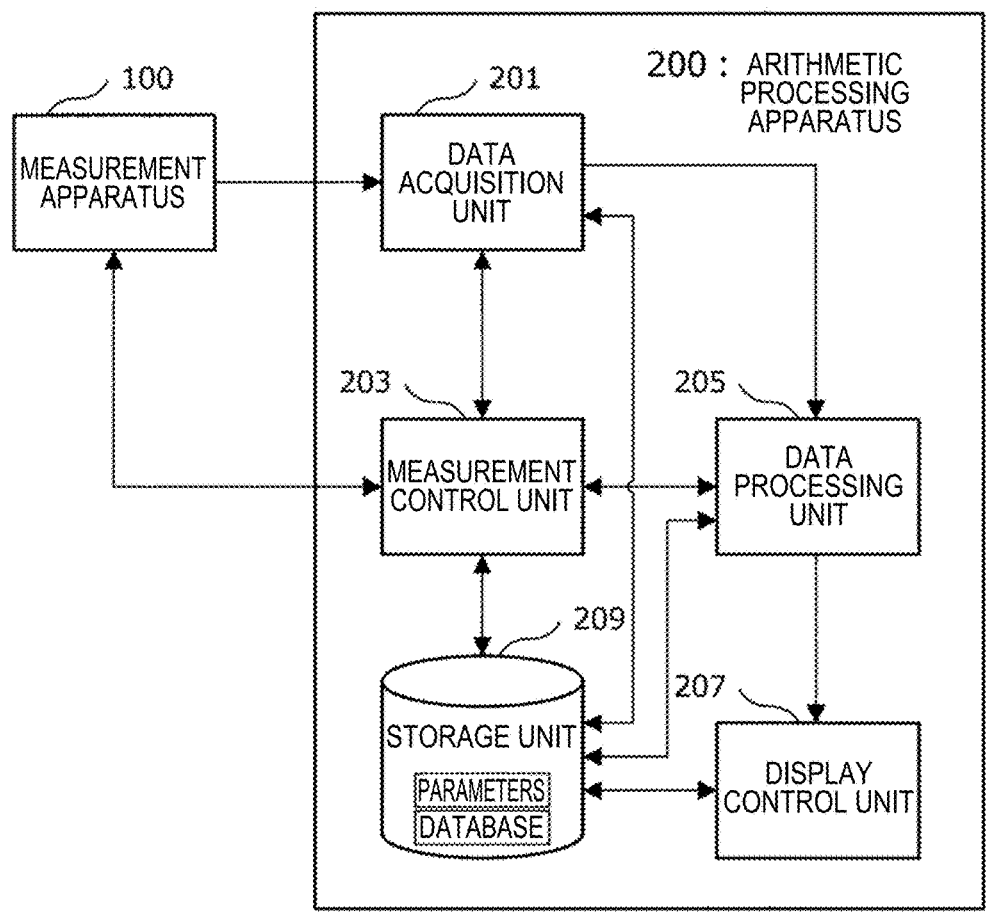
FIG. 5 is a block diagram illustrating an example of a configuration of an arithmetic processing apparatus included in a shape inspection apparatus according to the embodiment.

Now, a configuration of the arithmetic processing apparatus 200 included in the shape inspection apparatus 10 according to the present embodiment will be described in detail with reference to FIG. 5. FIG. 5 is a block diagram illustrating an example of an overall configuration of the arithmetic processing apparatus 200 according to the present embodiment.

The arithmetic processing apparatus 200 according to the present embodiment is an apparatus that calculates information for inspection used for shape inspection of the metallic body S, on the basis of luminance values of reflected light obtained by the measurement apparatus 100. In the arithmetic processing apparatus 200, at least information on an inclination of the surface of the metallic body S is calculated, and further, information on the surface shape of the metallic body S may be calculated, as the information for inspection.

As illustrated in FIG. 5, this arithmetic processing apparatus 200 mainly includes a data acquisition unit 201, a measurement control unit 203, a data processing unit 205, a display control unit 207, and a storage unit 209.

The data acquisition unit 201 is configured with, for example, a central processing unit (CPU), a read only memory (ROM), a random access memory (RAM), a communication device, and the like. The data acquisition unit 201 acquires data on luminance values of reflected light, which is generated and output by the measurement apparatus 100, and transmits the data to the data processing unit 205 described later. Moreover, the data acquisition unit 201 may contain the acquired data on the luminance values of the reflected light as history information in the storage unit 209 described later, in association with time information on date and time at which the data is acquired.

The measurement control unit 203 is configured with a CPU, a ROM, a RAM, a communication device, and the like. The measurement control unit 203 controls measurement of the metallic body S by the measurement apparatus 100 according to the present embodiment. Specifically, in starting the measurement of the metallic body S, the measurement control unit 203 sends controls signals for starting emission of illumination light beams to the plurality of illumination light sources (e.g., the first illumination light source 105, the second illumination light source 107, and the third illumination light source 109 in FIGS. 2A to 2C or FIG. 4).

When the plurality of illumination light sources start to irradiate the surface of the metallic body S with the illumination light beams, the measurement control unit 203 sends a trigger signal for starting measurement to the line sensor camera group 101, on the basis of a PLG signal that is sent at regular intervals from a driving mechanism etc. for changing a relative position between the metallic body S and the measurement apparatus 100 (e.g., a PLG signal output each time the metallic body S moves 1 mm).

In this manner, the measurement apparatus 100 can generate measurement data (data on luminance values of reflected light) at each position of the metallic body S in the conveyance direction.

The data processing unit 205 is configured with, for example, a CPU, a ROM, a RAM, a communication device, and the like. The data processing unit 205 uses data on luminance values of reflected light, generated by the measurement apparatus 100, to perform data processing, which will be described later, on the data on the luminance values of the reflected light beams, and calculates information for inspection used for shape inspection of the metallic body S. Upon ending the calculation process of information for inspection, the data processing unit 205 transmits information on the obtained processing results to the display control unit 207.

This data processing unit 205 will be described in detail later.

The display control unit 207 is configured with, for example, a CPU, a ROM, a RAM, an output device, and the like. The display control unit 207 performs display control in displaying various processing results including calculation results of information for inspection on the metallic body S, which are transmitted from the data processing unit 205, on an output device (e.g., a display) included in the arithmetic processing apparatus 200, an output device provided outside the arithmetic processing apparatus 200, or the like. Thus, a user of the shape inspection apparatus 10 can recognize on-site various processing results, such as information for inspection on the metallic body S.

The storage unit 209 is configured with, for example, a RAM, a storage device, and the like included in the arithmetic processing apparatus 200 according to the present embodiment. In the storage unit 209, various parameters and process intermediate progresses that the arithmetic processing apparatus 200 according to the present embodiment needs to save when performing some sort of process, various databases and programs, or the like are recorded as appropriate. With regard to this storage unit 209, the data acquisition unit 201, the measurement control unit 203, the data processing unit 205, the display control unit 207, and the like can perform a data read/write process freely.

[Data Processing Unit 205]

Next, a configuration of the data processing unit 205 included in the arithmetic processing apparatus 200 according to the present embodiment will be described in detail with reference to FIGS. 6 to 8.

Figure 6:
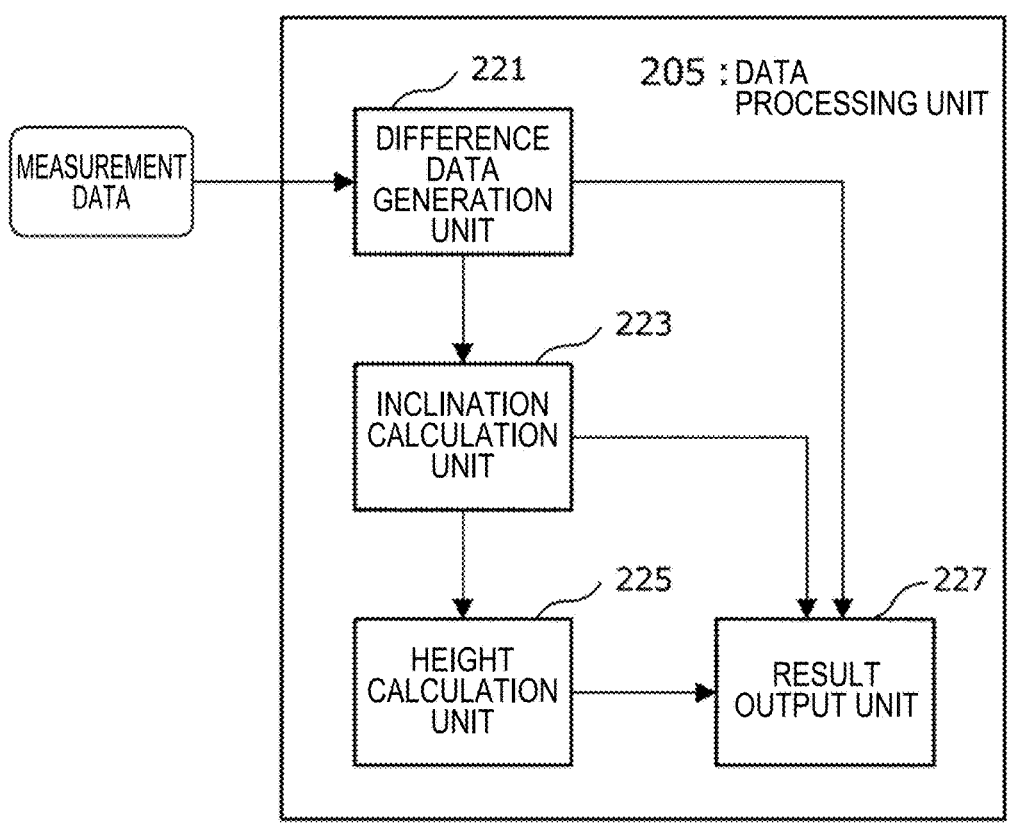
FIG. 6 is a block diagram illustrating an example of a configuration of a data processing unit included in an arithmetic processing apparatus according to the embodiment.

FIG. 6 is a block diagram illustrating an example of a configuration of a data processing unit included in an arithmetic processing apparatus according to the present embodiment. FIG. 7 is an explanatory diagram for explaining a method for selecting reflected light in a shape inspection apparatus according to the present embodiment. FIG. 8 is a graph diagram for explaining the relation between an inclination in the conveyance direction and a difference value of measured luminance values.

The data processing unit 205 according to the present embodiment selects, from among data on luminance values of reflected light of a plurality of illumination light beams, which are measured by the measurement apparatus 100, one piece of data on a luminance value of reflected light of illumination light installed in the upstream direction of the metallic body S with respect to the line sensor camera group 101, and one piece of data on a luminance value of reflected light of illumination light installed in the downstream direction of the metallic body S with respect to the line sensor camera group 101. The selected two pieces of data are, in other words, data on two luminance values derived from two illumination light sources that are provided to face each other with the line sensor camera group 101 therebetween in a relative movement direction. After that, the data processing unit 205 calculates information for inspection including at least information on an inclination of the surface of the metallic body S, on the basis of a difference (i.e., a luminance difference) between the data on the two luminance values selected in the above-described manner. As illustrated in FIG. 6, this data processing unit 205 includes a difference data generation unit 221, an inclination calculation unit 223, a height calculation unit 225, and a result output unit 227.

The difference data generation unit 221 is configured with, for example, a CPU, a ROM, a RAM, and the like. The difference data generation unit 221 selects data on two luminance values, according to properties etc. of the metallic body S, from among data on luminance values of reflected light of a plurality of illumination light beams (in the following direction, data on a luminance value of reflected light of n-th illumination light is simply called "measurement data on n-th illumination light") acquired by the data acquisition unit 201. After that, the difference data generation unit 221 performs a difference data generation process (i.e., a luminance difference data generation process), which will be described later, on the selected measurement data on the two luminance values.

Hereinafter, the difference data generation process performed by the difference data generation unit 221 will be described.

As described above, the difference data generation unit 221 first selects measurement data on two luminance values used for calculation of difference data. Two examples of a criterion for selection of measurement data are given below.

A first selection criterion is a method based on a reflection spectrum of the metallic body S. In the case where the metallic body S is colored, an amount of luminance fluctuation increases for a wavelength influenced by the coloring. In performing a process of calculating a difference between the selected measurement data on the two luminance values, the difference data generation unit 221 preferably refrains from using measurement data with a large amount of fluctuation in luminance value caused by a factor other than fluctuation in the shape of the metallic body S, in order to ensure precision of the calculated difference. Hence, if a reflection spectrum of the metallic body S is known beforehand, two pieces of measurement data may be selected before the difference calculation process, regarding a combination of most equivalent reflection spectrum intensities.

Figure 7:
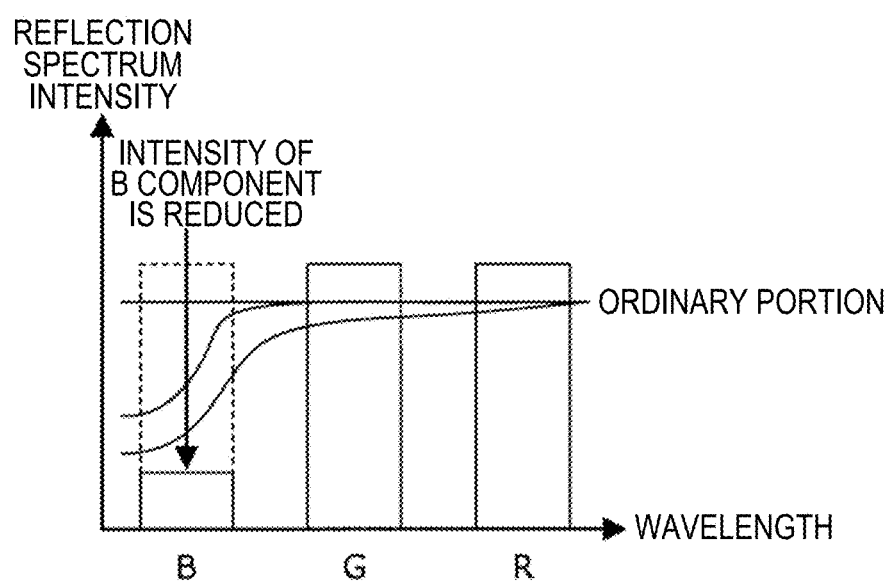
FIG. 7 is an explanatory diagram for explaining a method for selecting reflected light in a shape inspection apparatus according to the embodiment.

For example, the difference data generation unit 221 refers to measurement data on a plurality of luminance values each time the measurement data is output from the data acquisition unit 201, and when the amount of fluctuation of measurement data on a luminance value that is obtained from blue light used as illumination light becomes equal to or larger than a predetermined threshold value as illustrated in FIG. 7, decides not to use measurement data on blue light. On this occasion, in the case where three types of illumination light sources are installed in the measurement apparatus 100 as illustrated in FIGS. 2A to 2C or FIG. 4, the difference data generation unit 221 decides to use measurement data other than measurement data on blue light (i.e., measurement data on red light and measurement data on green light).

A second selection criterion is a method using an in-plane average value of luminance differences, obtained by actually calculating luminance differences regarding measurement data on luminance values that may be selected, which method may be used in the case where the measurement apparatus 100 has the arrangement illustrated in FIG. 2A. In the arrangement illustrated in FIG. 2A, the luminance difference is an inclination of the surface of the metallic body S along the conveyance direction, and the in-plane average value of luminance differences (the average value of luminance differences in the surface of the metallic body S) is zero if the average height of the metallic body S is constant. Accordingly, this process of calculating the in-plane average value is preferably performed on an area sufficiently larger than the size of a shape change that may occur in the metallic body S. Assume that a portion having a different color tone from other portions is present at the surface of the metallic body S to be inspected. In such a case, at the portion with a color tone change, light of a wavelength band corresponding to a complementary color of the color tone is absorbed, so that measurement data (i.e., reflection intensity) on a luminance value of the corresponding wavelength band changes relative to other portions. For example, in the case where the metallic body S to be inspected is a steel plate subjected to a pickling step in steel plate production, long pickling time causes yellow coloring called yellowing. Assuming that a yellow portion is present in the metallic body S to be inspected, the light-band intensity of blue, which is a complementary color of yellow, is reduced as illustrated in FIG. 7. In this case, when luminance differences from measurement data on other luminance values are calculated, the differences get out of balance and the average value of luminance differences does not become close to zero. Hence, the difference data generation unit 221 actually calculates luminance differences regarding all combinations of measurement data on luminance values that may be selected, and calculates the average value of the calculated luminance differences. Then, the difference data generation unit 221 selects a combination that makes the average value of luminance differences closest to zero (e.g., a combination of measurement data on green light and measurement data on red light in FIG. 7) at constant intervals, e.g., every image capturing frame.

When having selected measurement data used for processing, the difference data generation unit 221 may notify the measurement control unit 203 of information on measurement data that is not used. Upon receiving such a notification, the measurement control unit 203 may turn off or reduce illumination intensity of an illumination light source that provides measurement data that is not used for processing, in order to reduce power consumption.

Upon selecting measurement data on luminance values used for calculation of difference data, the difference data generation unit 221 generates difference data (i.e., luminance difference data) obtained by subtracting a luminance value of one of the selected two pieces of measurement data from a luminance value of the other piece of measurement data. Measurement data on luminance values of reflected light, generated by the measurement apparatus 100, can actually be recognized as a captured image of reflected light, but the generation of difference data is performed for each pixel constituting each piece of measurement data.

By performing such a difference arithmetic process, the difference data generation unit 221 can obtain a data group of difference values (in other words, map data on difference values) for the entire surface of the metallic body S. The data group of difference values obtained in this manner serves as information for inspection used in inspecting the shape (specifically, surface shape) of the metallic body S. Moreover, the information for inspection can be imaged by replacing difference values included in the information for inspection with high/low of luminance values or light/dark. By imaging the generated map data on luminance differences into a difference image, shape inspection based on the difference image can be performed.

There is not particular limitation on which piece of measurement data is subtracted from the other piece of measurement data, as long as it is consistent throughout the processing. That is, difference data may be obtained by subtracting measurement data on illumination light B from measurement data on illumination light A, or difference data may be obtained by subtracting measurement data on illumination light A from measurement data on illumination light B.

Here, difference data may be calculated in a manner that a luminance difference is zero when a flat object is measured with predetermined illumination intensity. Specifically, when measurement data on illumination light A is denoted by $I_A$ and measurement data on illumination light B is denoted by $I_B$, difference data D is expressed by the following formula 101 or formula 103, for example.

$$D = k_1 \times I_A - k_2 \times I_B \quad \text{(formula 101)}$$

$$D = I_A - I_B + \Delta I \quad \text{(formula 103)}$$

Here, in the above formula 101, $k_1$ and $k_2$ are positive coefficients, and may be decided in advance in a manner that D is zero when a flat object is measured. Alternatively, for simplicity, $k_1$ and $k_2$ may each be set to 1, and illumination intensity of each color may be set in advance in a manner that D is zero.

The above formula 103 is an example of calculating the difference data D by using a correction constant $\Delta I$ instead of the coefficients $k_1$ and $k_2$. Here, as in the case of using the coefficients $k_1$ and $k_2$, the correction constant $\Delta I$ may be decided in advance in a manner that D is zero when a flat object is measured.

Information on values of the coefficients $k_1$ and $k_2$ or a value of the correction constant $\Delta I$ decided in advance is contained in the storage unit 209, for example. In performing the difference data generation process, the difference data generation unit 221 acquires the information on values of the coefficients $k_1$ and $k_2$ or a value of the correction constant $\Delta I$ from the storage unit 209, and performs the difference data generation process.

Reflectance fluctuation without wavelength dependence, due to soil etc. other than discoloration, equally influences $I_A$ and $I_B$; hence, the difference data generation process as described above performed by the difference data generation unit 221 removes the influence of a reflectance difference without wavelength dependence from measurement data, making it possible to precisely detect a microscopic shape.

The difference data generation unit 221 outputs the difference data (luminance difference data) generated in the above-described manner to the inclination calculation unit 223. In addition, the difference data generation unit 221 may output the generated difference data itself to the result output unit 227.

The inclination calculation unit 223 is configured with, for example, a CPU, a ROM, a RAM, and the like. The inclination calculation unit 223 calculates the direction and magnitude of an inclination of the surface of the metallic body S, on the basis of the relation between a luminance difference and an inclination, by using the difference data (luminance difference data) output from the difference data generation unit 221. Hereinafter, a method for calculating inclination by the inclination calculation unit 223 will be described specifically with reference to FIG. 8.

In the measurement apparatus 100 according to the present embodiment, at least two illumination light sources are installed (fixed) in a manner that their optical axes form substantially equal angles with a normal direction to the surface of the metallic body S, as illustrated in FIGS. 2B, 3, 4, and the like. This angle will be called a light source angle $\theta$. Since the illumination light sources are installed in this manner, when images of a plane that is kept level are captured, a luminance difference between one measured luminance selected from among measured luminances of reflected light detected by the line sensor camera group 101 and the other measured luminance can be regarded as zero. Here, when an inclination tamp in the longitudinal direction of the metallic body S occurs in a plane that is kept level, the degrees of reflection of illumination light beams change, causing a change in a luminance difference between reflected light beams.

Figure 8:
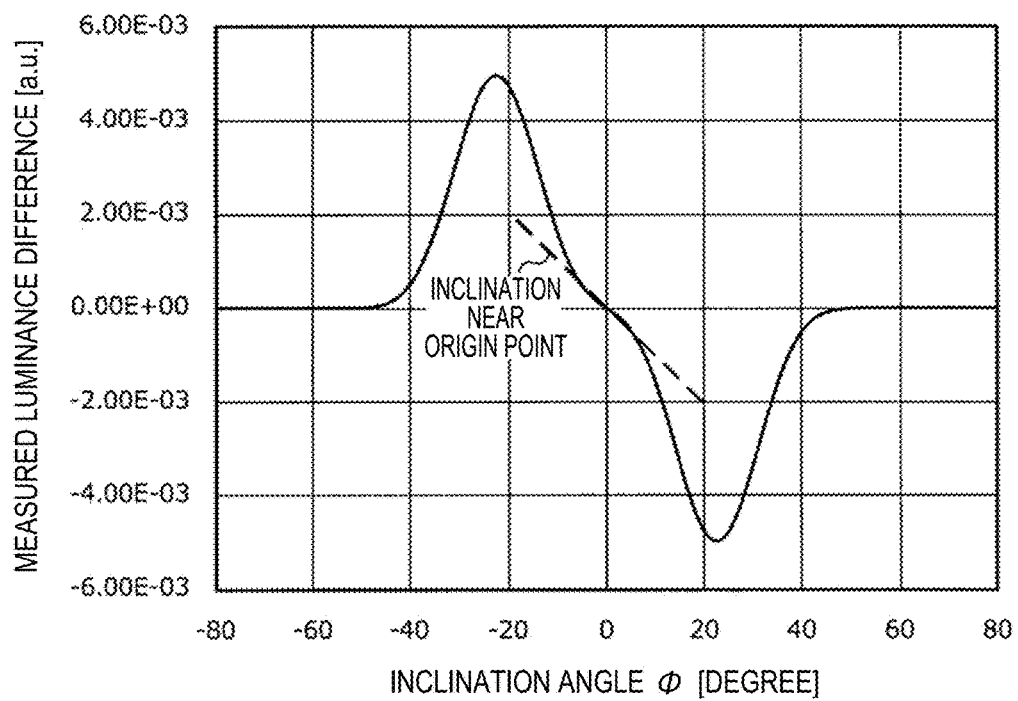
FIG. 8 is a graph diagram for explaining the relation between an inclination in the conveyance direction and a difference value of measured luminance values.
Figure 9:
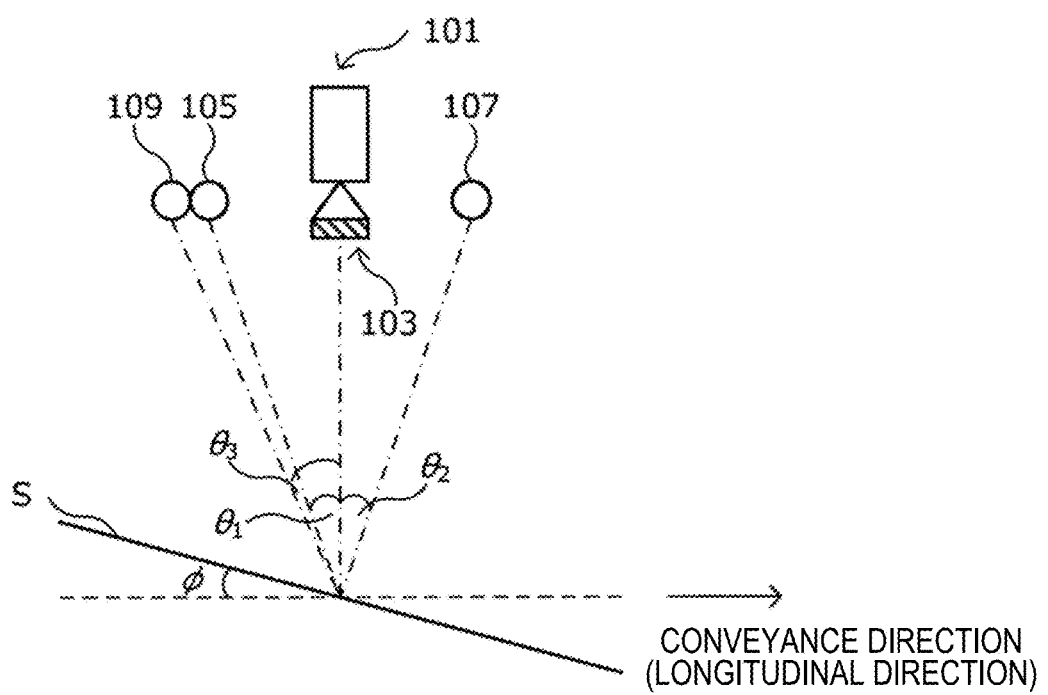
FIG. 9 is an explanatory diagram schematically illustrating the relation between a light source angle of an illumination light source and an inclination angle of a surface in a measurement apparatus according to the embodiment.

A measurement object that is known not to have unevenness on its surface is subjected to measurement while an inclination angle $\varphi$ is changed, and how difference data changes in one given pixel is calculated and shown in FIG. 8. In FIG. 8, the horizontal axis corresponds to the inclination angle $\varphi$, and the vertical axis corresponds to a difference value of measured luminance values. As schematically illustrated in FIG. 9, the inclination angle $\varphi$ of the surface is different from the light source angle $\theta$. Here, the light source angle $\theta$ was set to 45 degrees in obtaining the graph diagram of FIG. 8.

Luminance difference data shown in FIG. 8 reveals correlation between the inclination angle $\varphi$ and the luminance difference. Hence, in the arithmetic processing apparatus 200 according to the present embodiment, a luminance difference calculated by the difference data generation unit 221 is converted into an inclination angle, according to the relation between the inclination angle and the luminance difference shown in FIG. 8, for example. Specifically, a conversion coefficient for converting a luminance difference into an angle is decided according to an inclination of the graph near the origin point, i.e., in the vicinity of an inclination of zero degrees, in FIG. 8. This conversion coefficient is changed also by aperture of shift lenses provided in the line sensor camera group 101, or the like; hence, the conversion coefficient is decided experimentally in advance by using an optical system used for actual measurement.

FIG. 8 reveals that when the inclination of the graph near the origin point (i.e., the conversion coefficient) is denoted by a, a luminance difference $\Delta L$ and the inclination angle $\varphi$ can be expressed by a relation of $\Delta L = \alpha \times \varphi$. Hence, the inclination calculation unit 223 can convert luminance differences $\Delta L$ into inclination angles $\varphi$ of the surface by using a data group on $\Delta L$ output from the difference data generation unit 221, and the conversion coefficient $\alpha$. The inclination of the surface of the metallic body S of interest corresponds to a tangent at the inclination angle $\varphi$ obtained by converting the luminance difference. Hence, the inclination calculation unit 223 calculates tamp, which is the tangent at the calculated inclination angle $\varphi$, thereby calculating the inclination of the surface of the metallic body S of interest. The inclination calculated in this manner expresses the direction of the inclination by its sign, and expresses the specific magnitude of the inclination by its absolute value.

Information on the conversion coefficient decided in advance is contained in the storage unit 209, for example. In performing the inclination calculation process, the inclination calculation unit 223 acquires the information on the conversion coefficient from the storage unit 209, and converts the luminance difference into the inclination angle.

By performing the above-described process for all elements of the luminance difference data, the inclination calculation unit 223 can obtain a data group of inclination values (in other words, map data on inclination values) for the entire surface of the metallic body S. The data group of inclination values obtained in this manner serves as information for inspection used in inspecting the shape (specifically, surface shape) of the metallic body S. Moreover, the information for inspection can be imaged by replacing inclination values included in the information for inspection with high/low of luminance values or light/dark. By imaging the generated map data on inclinations into an inclination image, shape inspection based on the inclination image can be performed.

Moreover, the inclination calculation unit 223 can perform inspection of the surface shape of the metallic body S by comparing the calculated inclination with a predetermined threshold value. That is, a threshold value of the inclination of the surface when an abnormal portion is present at the surface of the metallic body S is specified in advance by performing known statistical processing or the like on the basis of operation data in the past, etc., and contained in the storage unit 209 or the like. Then, the inclination calculation unit 223 specifies the magnitude relation between the calculated inclination value and the threshold value, which makes it possible to inspect whether an abnormal portion is present at the surface of the metallic body S of interest.

The inclination calculation unit 223 outputs the data on an inclination of the surface of the metallic body S generated in the above-described manner to the height calculation unit 225. In addition, the inclination calculation unit 223 may output the generated data on an inclination of the surface of the metallic body S itself, or inspection results of the surface of the metallic body S to the result output unit 227.

The relation between the value of difference data and the inclination angle as shown in FIG. 8 may be obtained by utilizing actually measured values, or may be generated by simulation by utilizing known various reflection models, such as Kirchhoff-Beckmann-Spizzichino model, Torrance-Sparrow-Beckman model, Phone model, and Bline model.

The height calculation unit 225 is configured with, for example, a CPU, a ROM, a RAM, and the like. The height calculation unit 225 calculates the height of the surface of the metallic body S of interest by using the inclination of the surface of the metallic body S calculated by the inclination calculation unit 223. Specifically, the height calculation unit 225 integrates the inclination tamp of the surface of the metallic body S calculated by the inclination calculation unit 223 along the relative movement direction of the monochrome line sensor cameras and the metallic body S (i.e., the longitudinal direction of the metallic body S (conveyance direction)), thereby calculating the height of the surface of the metallic body S.

By performing the above-described integrating process for all elements of the data on the inclinations of the surface, the height calculation unit 225 can obtain a data group on surface heights (in other words, map data on surface heights) for the entire surface of the metallic body S. The data group on surface heights obtained in this manner serves as information for inspection used in inspecting the shape (specifically, surface shape) of the metallic body S. Moreover, the information for inspection can be imaged by replacing surface height values included in the information for inspection with high/low of luminance values or light/dark. By imaging the generated map data on surface heights into a height image, shape inspection based on the height image can be performed.

The height calculation unit 225 outputs the data on the height of the surface of the metallic body S generated in the above-described manner to the result output unit 227.

The result output unit 227 is configured with, for example, a CPU, a ROM, a RAM, and the like. The result output unit 227 outputs various types of information on shape inspection results of the metallic body, such as luminance difference data generated by the difference data generation unit 221, data on the inclination of the surface of the metallic body S or inspection results calculated by the inclination calculation unit 223, and data on the height of the surface of the metallic body S calculated by the height calculation unit 225, to the display control unit 207. Thus, various types of information on shape inspection results of the metallic body S is output to a display unit (not illustrated). The result output unit 227 may also output the obtained shape inspection results to an external device such as a process computer system for production management, and may create various record files relevant to products by utilizing the obtained shape inspection results. Moreover, the result output unit 227 may contain information on the shape inspection results of the metallic body S, as history information, in the storage unit 209 or the like, in association with time information on date and time at which the information is calculated.

An example of the function of the arithmetic processing apparatus 200 according to the present embodiment has been illustrated. Each of the above structural elements may be configured with a general-purpose member or circuit, and may be configured with hardware specialized for the function of each structural element. A CPU or the like may perform all of the functions of respective structural elements. Thus, a utilized configuration can be changed as appropriate, according to the technology level at the time of performing the present embodiment.

Note that the computer program for providing each function of the arithmetic processing apparatus according to the above present embodiment can be created and implemented in a personal computer or the like. Moreover, a computer-readable recording medium that contains this computer program can be provided as well. For example, the recording medium is a magnetic disk, an optical disc, a magneto-optical disk, a flash memory, or the like. The above computer program may be delivered via a network for example, without using the recording medium.

(Sequence of Shape Inspection Method)

Figure 10:
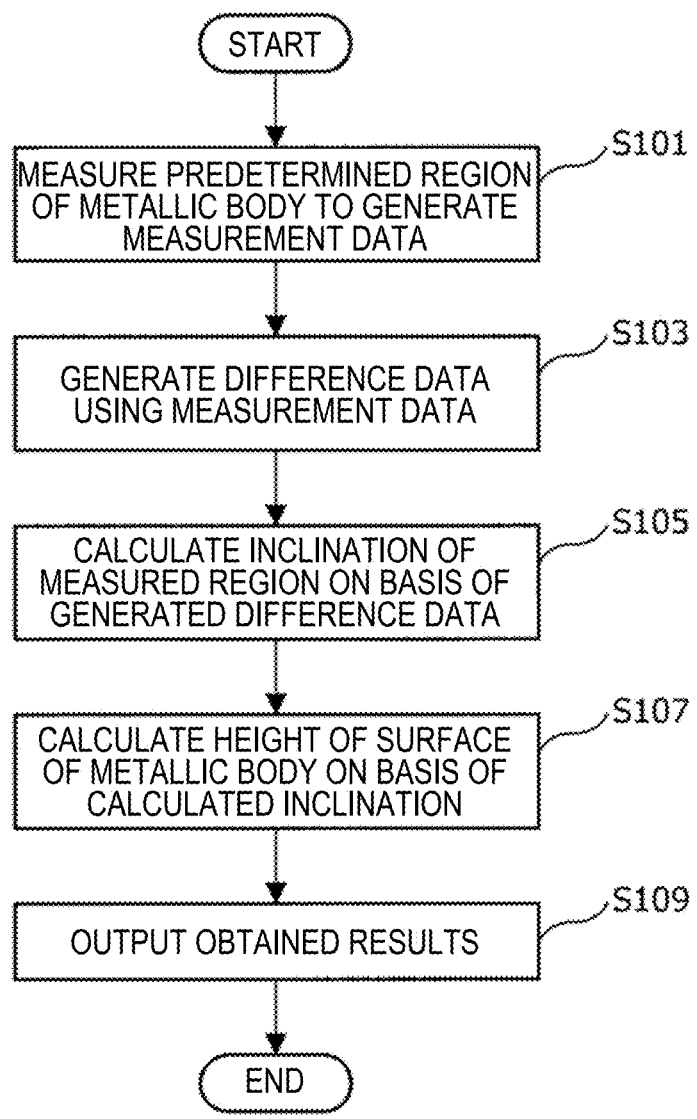
FIG. 10 is a flowchart showing an example of a sequence of a shape inspection method according to the embodiment.

Now, an example of a sequence of a shape inspection method performed in the shape inspection apparatus 10 according to the present embodiment will be described briefly with reference to FIG. 10. FIG. 10 is a flowchart showing an example of a sequence of a shape inspection method according to the present embodiment.

The measurement apparatus 100 of the shape inspection apparatus 10, under control of the measurement control unit 203 of the arithmetic processing apparatus 200, measures a predetermined region of the surface of the metallic body S by using a plurality of illumination light beams to generate measurement data on respective illumination light beams (step S101). After that, the measurement apparatus 100 outputs the generated measurement data to the arithmetic processing apparatus 200.

Upon acquiring the measurement data output from the measurement apparatus 100, the data acquisition unit 201 of the arithmetic processing apparatus 200 outputs the acquired measurement data to the difference data generation unit 221 of the data processing unit 205.

The difference data generation unit 221 of the data processing unit 205 selects two pieces of measurement data used for processing from among measurement data on the plurality of illumination light beams by the method described above, and then generates difference data (i.e., luminance difference data) (step S103). After that, the difference data generation unit 221 outputs the generated luminance difference data to the inclination calculation unit 223.

The inclination calculation unit 223 calculates data on an inclination of the surface of the metallic body S of interest (i.e., an inclination of the measured region) by using difference data (luminance difference data) output from the difference data generation unit 221 (step S105). After that, the inclination calculation unit 223 outputs the calculated data on inclination to the height calculation unit 225.

After that, the height calculation unit 225 integrates inclinations contained in the data on inclination output from the inclination calculation unit 223, thereby calculating the height of the surface of the metallic body (step S107). The height calculation unit 225 outputs the obtained data on the height of the surface of the metallic body to the result output unit 227.

When various types of information for inspection used for surface inspection of the metallic body S is input, the result output unit 227 outputs the obtained results to a user or various devices provided outside (step S109). Thus, the user can recognize inspection results on the shape of the metallic body S.

An example of a shape inspection method performed in the shape inspection apparatus 10 according to the present embodiment has been described briefly with reference to FIG. 10.

(Hardware Configuration)

Figure 11:
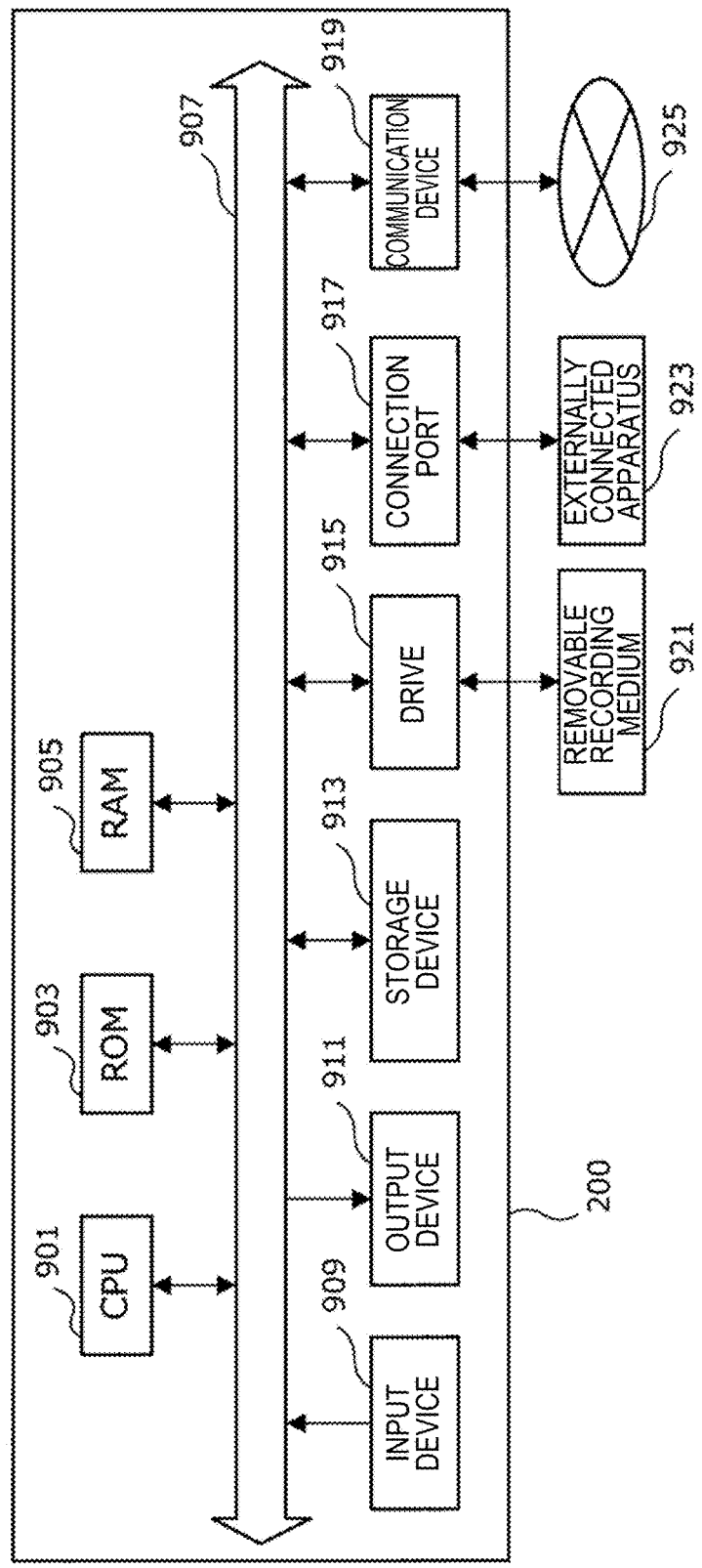
FIG. 11 is a block diagram illustrating an example of a hardware configuration of an arithmetic processing apparatus according to the embodiment.

Next, the hardware configuration of the arithmetic processing apparatus 200 according to an embodiment of the present invention will be described in detail with reference to FIG. 11. FIG. 11 is a block diagram for explaining the hardware configuration of the arithmetic processing apparatus 200 according to an embodiment of the present invention.

The arithmetic processing apparatus 200 mainly includes a CPU 901, a ROM 903, and a RAM 905. Furthermore, the arithmetic processing apparatus 200 also includes a bus 907, an input device 909, an output device 911, a storage device 913, a drive 915, a connection port 917, and a communication device 919.

The CPU 901 serves as a central processing apparatus and a control device, and controls the overall operation or a part of the operation of the arithmetic processing apparatus 200 according to various programs recorded in the ROM 903, the RAM 905, the storage device 913, or a removable recording medium 921. The ROM 903 stores programs, operation parameters, and the like used by the CPU 901. The RAM 905 primarily stores programs that the CPU 901 uses and parameters and the like varying as appropriate during the execution of the programs. These are connected with each other via the bus 907 configured from an internal bus such as a CPU bus or the like.

The bus 907 is connected to the external bus such as a PCI (Peripheral Component Interconnect/Interface) bus via the bridge.

The input device 909 is an operation means operated by a user, such as a mouse, a keyboard, a touch panel, buttons, a switch and a lever. The input device 909 may be a remote control means (a so-called remote control) using, for example, infrared light or other radio waves, or may be an externally connected apparatus 923 such as a PDA conforming to the operation of the arithmetic processing apparatus 200. Furthermore, the input device 909 generates an input signal based on, for example, information which is input by a user with the above operation means, and is configured from an input control circuit for outputting the input signal to the CPU 901. The user can input various data to the shape inspection apparatus 10 and can instruct the shape inspection apparatus 10 to perform processing by operating this input device 909.

The output device 911 is configured from a device capable of visually or audibly notifying acquired information to a user. Examples of such device include display devices such as a CRT display device, a liquid crystal display device, a plasma display device, an EL display device and lamps, audio output devices such as a speaker and a headphone, a printer, a mobile phone, a facsimile machine, and the like. For example, the output device 911 outputs a result obtained by various processes performed by the arithmetic processing apparatus 200. More specifically, the display device displays, in the form of texts or images, a result obtained by various processes performed by the arithmetic processing apparatus 200. On the other hand, the audio output device converts an audio signal such as reproduced audio data and sound data into an analog signal, and outputs the analog signal.

The storage device 913 is a device for storing data configured as an example of a storage unit of the arithmetic processing apparatus 200 and is used to store data. The storage device 913 is configured from, for example, a magnetic storage device such as a HDD (Hard Disk Drive), a semiconductor storage device, an optical storage device, or a magneto-optical storage device. This storage device 913 stores programs to be executed by the CPU 901, various data, and various data obtained from the outside.

The drive 915 is a reader/writer for recording medium, and is embedded in the arithmetic processing apparatus 200 or attached externally thereto. The drive 915 reads information recorded in the attached removable recording medium 921 such as a magnetic disk, an optical disk, a magneto-optical disk, or a semiconductor memory, and outputs the read information to the RAM 905. Furthermore, the drive 915 can write in the attached removable recording medium 921 such as a magnetic disk, an optical disk, a magneto-optical disk, or a semiconductor memory. The removable recording medium 921 is, for example, a CD medium, a DVD medium, or a Blu-ray medium. The removable recording medium 921 may be a CompactFlash (CF; registered trademark), a flash memory, an SD memory card (Secure Digital Memory Card), or the like. Alternatively, the removable recording medium 921 may be, for example, an IC card (Integrated Circuit Card) equipped with a non-contact IC chip or an electronic device.

The connection port 917 is a port for allowing devices to directly connect to the arithmetic processing apparatus 200. Examples of the connection port 917 include a USB (Universal Serial Bus) port, an IEEE1394 port, a SCSI (Small Computer System Interface) port, an RS-232C port, and the like. By the externally connected apparatus 923 connecting to this connection port 917, the arithmetic processing apparatus 200 directly obtains various data from the externally connected apparatus 923 and provides various data to the externally connected apparatus 923.

The communication device 919 is a communication interface configured from, for example, a communication device for connecting to a communication network 925. The communication device 919 is, for example, a wired or wireless LAN (Local Area Network), Bluetooth (registered trademark), a communication card for WUSB (Wireless USB), or the like. Alternatively, the communication device 919 may be a router for optical communication, a router for ADSL (Asymmetric Digital Subscriber Line), a modem for various communications, or the like. This communication device 919 can transmit and receive signals and the like in accordance with a predetermined protocol such as TCP/IP on the Internet and with other communication devices, for example. The communication network 925 connected to the communication device 919 is configured from a network and the like, which is connected via wire or wirelessly, and may be, for example, the Internet, a home LAN, infrared communication, radio wave communication, satellite communication, or the like.

Heretofore, an example of the hardware configuration capable of realizing the functions of the arithmetic processing apparatus 200 according to an embodiment of the present invention has been shown. Each of the structural elements described above may be configured using a general-purpose material, or may be configured from hardware dedicated to the function of each structural element. Accordingly, the hardware configuration to be used can be changed as appropriate according to the technical level at the time of carrying out the present embodiment.

(Conclusion)

As described above, in a shape inspection apparatus and a shape inspection method for a metallic body according to an embodiment of the present invention, a combination of illumination light sources used for shape inspection is selected appropriately, so that the surface shape of a metallic body can be inspected accurately. Moreover, in a shape inspection apparatus and a shape inspection method for a metallic body according to an embodiment of the present invention, information for inspection can be obtained for each pixel of a captured image captured by monochrome line sensor cameras, which enables shape inspection with very high density. Furthermore, in a shape inspection apparatus and a shape inspection method for a metallic body according to an embodiment of the present invention, information for inspection can be calculated by simple arithmetic as described above, which enables shape inspection with very high speed.

EXAMPLES

Now, the shape inspection apparatus 10 according to the present invention will be described specifically with specific examples. Here, Examples described below are merely examples of a shape inspection apparatus and a shape inspection method according to the present invention, and a shape inspection apparatus and a shape inspection method according to the present invention are not limited to Examples described below.

Example 1

Figure 12:
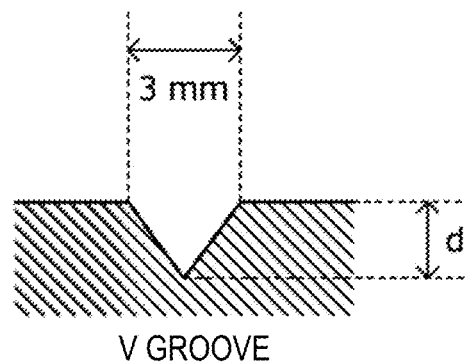
FIG. 12 is an explanatory diagram for explaining Example 1.

FIGS. 12 to 15 are explanatory diagrams for explaining Example 1. As illustrated in FIG. 12, in the present example, uneven shapes (V grooves) illustrated in FIG. 12 were intentionally formed on the surface of a steel plate, and shape measurement of the surface including the V grooves was tested. Here, widths of the V grooves were 3 mm, and depths d of the grooves were of four types, 50 µm, 100 µm, 200 µm, and 300 µm. In the steel plate, grooves with four types of depths were formed in the longitudinal direction of the steel plate.

As the shape inspection apparatus 10 according to the present invention, the shape inspection apparatus 10 including the measurement apparatus 100 illustrated in FIGS. 2A to 2C was used. Here, in the present example, green light (peak wavelength: 530 nm) was used as the first illumination light source 105, blue light (peak wavelength: 460 nm) was used as the second illumination light source 107, and red light (peak wavelength: 640 nm) was used as the third illumination light source 109. In the present example, as measurement data used in calculating a luminance difference, measurement data on green light serving as first illumination light and measurement data on blue light serving as second illumination light were used. Here, a transmission band of the band-pass filter 103a provided for the monochrome line sensor camera 101a for the first illumination light source 105 had a peak wavelength of 530 nm and a full width at half maximum of 60 nm. A transmission band of the band-pass filter 103b provided for the monochrome line sensor camera 101b for the second illumination light source 107 had a peak wavelength of 460 nm and a full width at half maximum of 60 nm. A transmission band of the band-pass filter 103c provided for the monochrome line sensor camera 101c for the third illumination light source 109 had a peak wavelength of 640 nm and a full width at half maximum of 60 nm.

The line sensor camera group 101 was installed perpendicularly to the surface of the steel plate, and $\theta_1$ and $\theta_2$ illustrated in FIG. 2A were each set to 45 degrees. The line sensor camera group 101 used in the present example had a resolution of 0.1 mm/pixel.

Using the shape inspection apparatus 10 as described above, the V grooves were measured on the basis of a difference between measured values of (green-blue).

To calculate an inclination from difference data values, a straight line expressed by y=−x was used for the following reason. The relation between a difference data value and an inclination as shown in FIG. 8 is obtained in the configuration of the measurement apparatus 100 in the present example, and it was determined that when attention is focused on the graph shape near the origin point, the graph shape can be approximated as a straight line of y=−x.

As a comparative example, the steel plate having the V grooves described above was inspected using a shape inspection apparatus by a light-section method, which is generally used, as disclosed in Patent Literature 1. Also in this light-section method, image capturing resolution was set to 0.1 mm, an installation angle of a laser linear light source was set to 45 degrees, and an installation angle of an area camera was set to 0 degrees.

Figure 13:
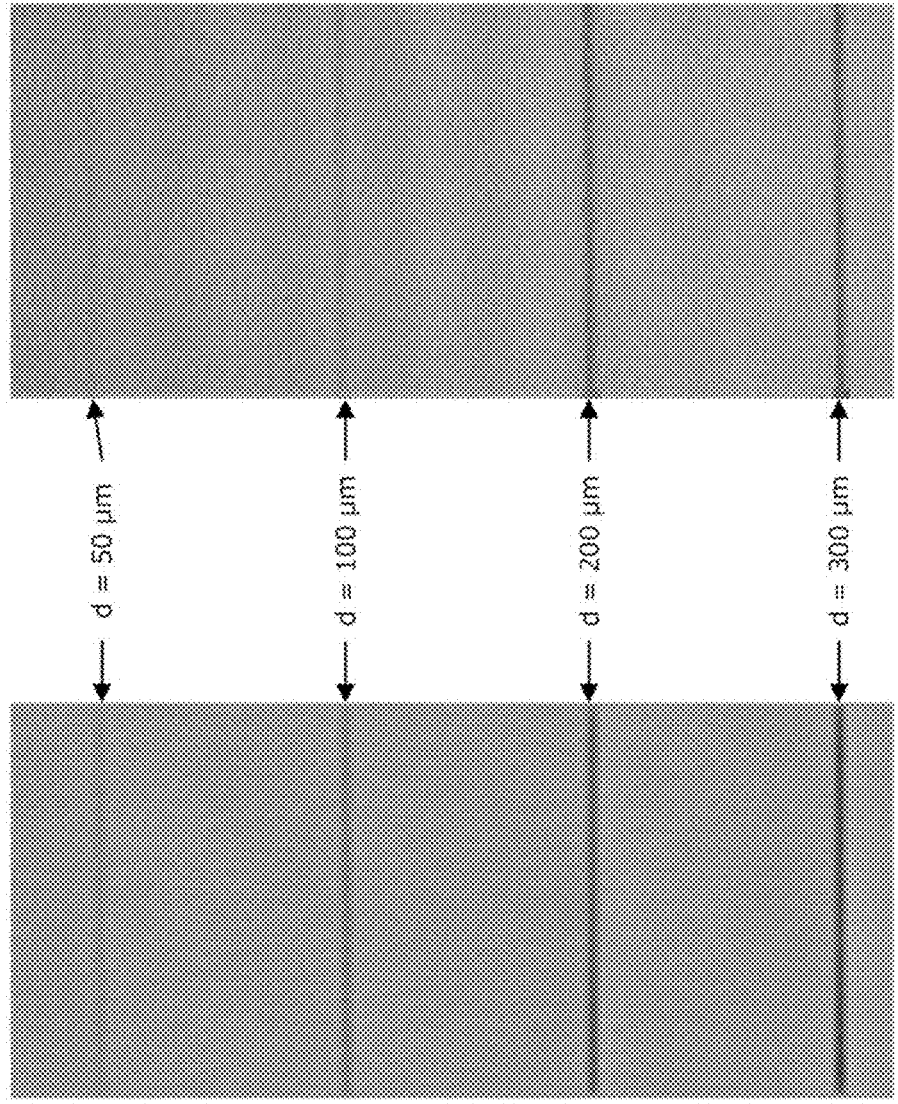
FIG. 13 is an explanatory diagram for explaining Example 1.

FIG. 13 shows a height image of the surface obtained by the shape inspection apparatus 10 according to the present invention (present invention example in FIG. 13) and a surface shape image obtained by the light-section method (comparative example in FIG. 13). FIG. 13 renders the height of the surface in a manner that a groove portion appears darker than a flat portion of the steel plate (in other words, in a manner that height corresponds to luminance), and shows height images obtained by setting a height of 0 mm to 128 and making a range of −400 µm to 400 µm correspond to 8-bit images of 0 to 255.

It is found from FIG. 13 that in both the present invention example and the comparative example, V groove portions corresponding to the four types of depths are darker than the surroundings in the captured images. On the other hand, when the captured image of the present invention example is compared with the captured image of the comparative example, it is found that the captured image of the present invention example has higher signal-noise ratio, which is particularly revealed by portions corresponding to d=50 µm and d=100 µm.

Figure 14:
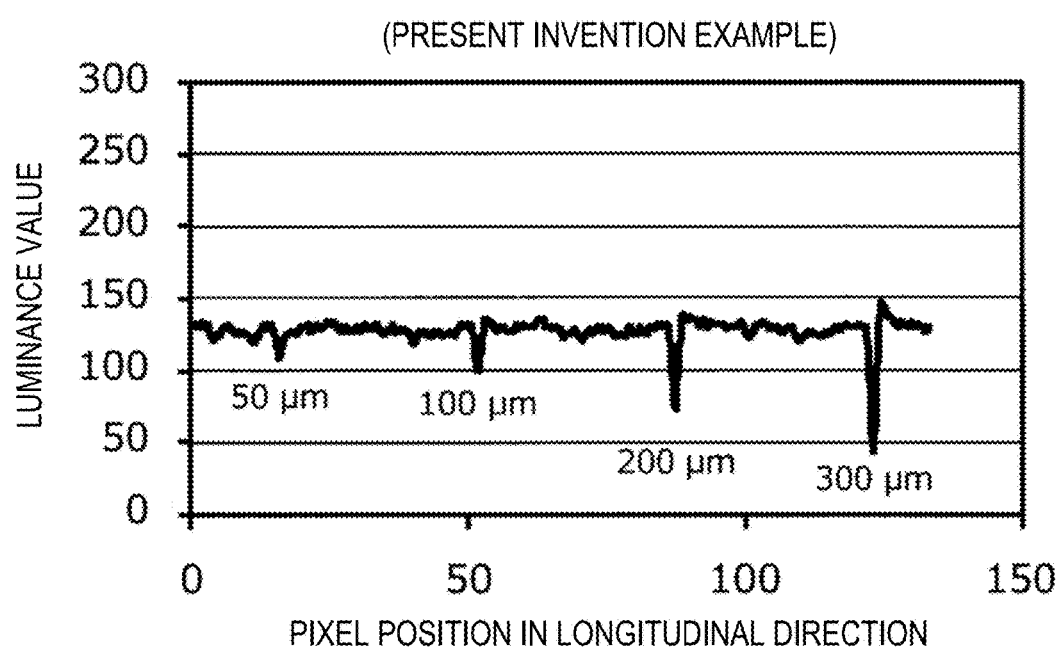
FIG. 14 is an explanatory diagram for explaining Example 1.
Figure 15:
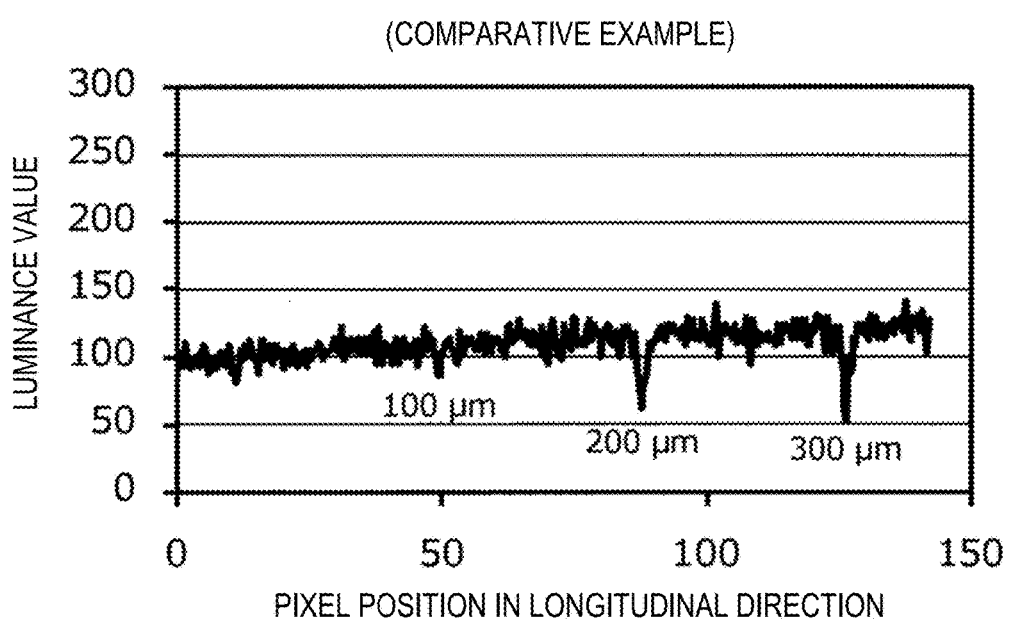
FIG. 15 is an explanatory diagram for explaining Example 1.

FIGS. 14 and 15 show graphs expressing the height of the surface at a given width-direction position (horizontal-direction position in FIG. 13) in the height images shown in FIG. 13. FIG. 14 reveals that in the present invention example, downwardly convex peaks are observed at pixel positions corresponding to the four types of V grooves. In contrast, FIG. 15 reveals that in the comparative example, peaks at positions corresponding to d=50 µm and d=100 µm are unclear. These results demonstrate that using the shape inspection apparatus 10 according to the present invention makes it possible to measure the height of the surface of the metallic body S precisely with high density.

Example 2

Figure 17:
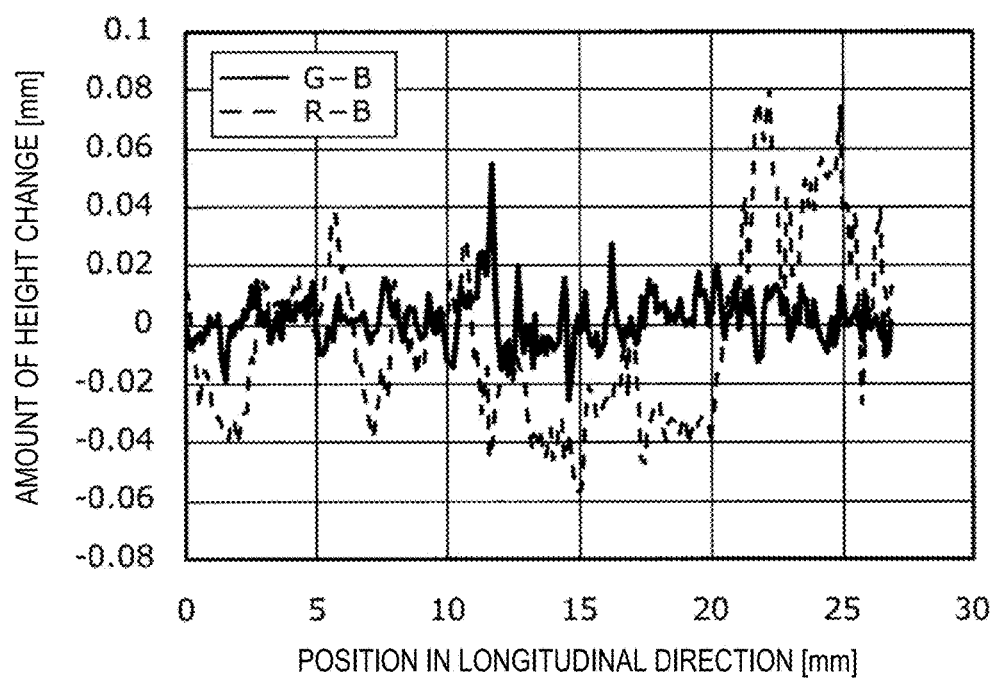
FIG. 17 is an explanatory diagram for explaining Example 2.

FIGS. 16 and 17 are explanatory diagrams for explaining Example 2. In Example 2 described below, a steel plate having flat red rust (rust whose main component is $Fe_2O_3$) on its surface was used as a sample, and shape inspection of a portion having red rust was tested. In Example 2, the shape inspection apparatus 10 according to the present invention used in Example 1 was used.

FIG. 16 shows captured images (i.e., measurement data on luminance values) obtained when illumination light beams are turned on individually. It is known that reflectance increases when red rust in the sample is observed using visible light with a wavelength of 550 nm or more. Consequently, when an image capturing process is performed using visible light with such a wavelength, a portion derived from red rust is shown brighter than the surroundings. Accordingly, a portion with a bright color observed in the image captured with the illumination light of 640 nm turned on, among the three types of captured images shown in FIG. 16, is a region where red rust has occurred. In the case where such a region having red rust is observed, the captured image captured using red light as illumination light corresponds to measurement data with a large amount of fluctuation in a reflection spectrum in the case described with reference to FIG. 7.

In the present example, a process of generating difference data of (G image-B image) and (R image-B image) was performed by using such three types of captured images to generate measurement data on two types of luminance differences, and measurement data on the height of the surface was calculated as in Example 1 by using the obtained measurement data on the luminance differences.

FIG. 17 shows the obtained results. In FIG. 17, the horizontal axis indicates a position in the longitudinal direction of the captured image in a portion having red rust, and the vertical axis indicates a height change of the surface of the steel plate.

FIG. 17 reveals that in surface height data based on a luminance difference of (R image-B image) calculated using measurement data with a large amount of fluctuation in a reflection spectrum, fluctuation in height change is large, indicating overlap of errors derived from the portion having red rust. In contrast, in surface height data based on a luminance difference of (G image-B image) calculated without using measurement data with a large amount of fluctuation in a reflection spectrum, fluctuation in height change is small. Here, the true height of the surface of the portion having red rust was additionally measured with a stylus roughness meter, which measurement revealed that the true height was extremely close to the surface height data based on the luminance difference of (G image-B image). These results demonstrated that focusing on a luminance difference calculated without using measurement data with a large amount of fluctuation in a reflection spectrum made it possible to measure the height of the sample surface more accurately.

The preferred embodiment(s) of the present invention has/have been described above with reference to the accompanying drawings, whilst the present invention is not limited to the above examples. A person skilled in the art may find various alterations and modifications within the scope of the appended claims, and it should be understood that they will naturally come under the technical scope of the present invention.

REFERENCE SIGNS LIST 10 shape inspection apparatus
100 measurement apparatus
101 line sensor camera group
103 band-pass filter
105 first illumination light source
107 second illumination light source
109 third illumination light source
200 arithmetic processing apparatus
201 data acquisition unit
203 measurement control unit
205 data processing unit
207 display control unit
209 storage unit
221 difference data generation unit
223 inclination calculation unit
225 height calculation unit
227 result output unit

The invention claimed is:

1. A shape inspection apparatus for a metallic body, comprising:
a measurement apparatus configured to irradiate a metallic body with at least two illumination light beams, and measure reflected light of the at least two illumination light beams from a same portion of the metallic body separately; and
an arithmetic processing apparatus configured to calculate information used for shape inspection of the metallic body on the basis of measurement results of luminance values of the reflected light obtained by the measurement apparatus, while controlling a measurement process by the measurement apparatus,
wherein the measurement apparatus includes
a plurality of illumination light sources configured to irradiate the metallic body with strip-shaped illumination light having mutually different peak wavelengths, and
a line sensor camera group composed of a plurality of monochrome line sensor cameras that are aligned vertically above a surface of the metallic body and set to capture images of the same portion of the metallic body by their respective shift lenses, the number of the monochrome line sensor cameras being the same as the number of the peak wavelengths of the illumination light emitted from the plurality of illumination light sources,
at least two of the plurality of illumination light sources are provided in a manner that a first angle formed by a normal direction to the surface of the metallic body and an optical axis of the first illumination light source is substantially equal to a second angle formed by the normal direction and an optical axis of the second illumination light source and the two illumination light sources face each other with the monochrome line sensor cameras therebetween in a relative movement direction of the metallic body and the measurement apparatus,
the monochrome line sensor cameras are provided with band-pass filters having transmitted wavelength bands corresponding to peak wavelengths of different illumination light sources among the plurality of illumination light sources, the band-pass filter being provided to precede an image sensor of the corresponding monochrome line sensor camera, and reflected light of illumination light from the illumination light source having a peak wavelength included in the transmitted wavelength band of the band-pass filter forms an image in each monochrome line sensor camera, and
the arithmetic processing apparatus calculates an inclination of the surface of the metallic body as the information by using a difference between a luminance value of the monochrome line sensor camera having the band-pass filter that transmits a peak wavelength of the first illumination light source with the highest transmittance and a luminance value of the monochrome line sensor camera having the band-pass filter that transmits a peak wavelength of the second illumination light source with the highest transmittance.

2. The shape inspection apparatus for the metallic body according to claim 1, wherein an illumination light source group composed of the plurality of illumination light sources configured to emit illumination light that forms images in the respective monochrome line sensor cameras of the line sensor camera group is provided at each of an upstream side and a downstream side along the relative movement direction with respect to the line sensor camera group.

3. The shape inspection apparatus for the metallic body according to claim 1, wherein the first angle and the second angle are each 30 degrees or more.

4. The shape inspection apparatus for the metallic body according to claim 1,
wherein the plurality of illumination light sources includes three or more illumination light sources, and
the arithmetic processing apparatus decides beforehand a combination of peak wavelengths of the illumination light that provides the reflected light used in calculating the difference on the basis of a reflection spectrum of the metallic body.

5. The shape inspection apparatus for the metallic body according to claim 1,
wherein the plurality of illumination light sources includes three or more illumination light sources, the illumination light source being arranged in a manner that a longitudinal direction of the illumination light source is substantially parallel to a width direction of the metallic body, and the arithmetic processing apparatus dynamically decides a combination of peak wavelengths of the illumination light that provides the reflected light used in calculating the difference in a manner that the combination makes an in-plane average value of the calculated differences closest to zero.

6. The shape inspection apparatus for the metallic body according to claim 1, wherein the arithmetic processing apparatus specifies a direction of the inclination on the basis of a sign of the difference and specifies a magnitude of the inclination on the basis of an absolute value of the difference.

7. The shape inspection apparatus for the metallic body according to claim 1, wherein the arithmetic processing apparatus further calculates a height of the surface of the metallic body as the information by integrating the calculated inclination of the surface of the metallic body along the relative movement direction of the monochrome line sensor cameras and the metallic body.

8. The shape inspection apparatus for the metallic body according to claim 1, wherein the arithmetic processing apparatus inspects the shape of the metallic body by comparing the calculated inclination of the surface of the metallic body with a predetermined threshold value.

9. A shape inspection method for a metallic body, comprising:
irradiating a metallic body with at least two illumination light beams, and measuring reflected light of the illumination light beams from the metallic body separately, by a measurement apparatus including a plurality of illumination light sources configured to irradiate the metallic body with strip-shaped illumination light having mutually different peak wavelengths, and a line sensor camera group composed of a plurality of monochrome line sensor cameras that are aligned vertically above a surface of the metallic body and set to capture images of a same portion of the metallic body by their respective shift lenses, the number of the monochrome line sensor cameras being the same as the number of the peak wavelengths of the illumination light emitted from the plurality of illumination light sources, wherein at least two of the plurality of illumination light sources are provided in a manner that a first angle formed by a normal direction to the surface of the metallic body and an optical axis of the first illumination light source is substantially equal to a second angle formed by the normal direction and an optical axis of the second illumination light source and the two illumination light sources face each other with the monochrome line sensor cameras therebetween in a relative movement direction of the metallic body and the measurement apparatus, and the monochrome line sensor cameras are provided with band-pass filters having transmitted wavelength bands corresponding to peak wavelengths of different illumination light sources among the plurality of illumination light sources, the band-pass filter being provided to precede an image sensor of the corresponding monochrome line sensor camera, and reflected light of illumination light from the illumination light source having a peak wavelength included in the transmitted wavelength band of the band-pass filter forms an image in each monochrome line sensor camera; and
calculating, by an arithmetic processing apparatus configured to calculate information for shape inspection of the metallic body on the basis of measurement results of luminance values of the reflected light obtained by the measurement apparatus, while controlling a measurement process by the measurement apparatus, an inclination of the surface of the metallic body as the information by using a difference between a luminance value of the monochrome line sensor camera having the band-pass filter that transmits a peak wavelength of the first illumination light source with the highest transmittance and a luminance value of the monochrome line sensor camera having the band-pass filter that transmits a peak wavelength of the second illumination light source with the highest transmittance.

10. The shape inspection method for the metallic body according to claim 9, wherein an illumination light source group composed of the plurality of illumination light sources configured to emit illumination light that forms images in the respective monochrome line sensor cameras of the line sensor camera group is provided at each of an upstream side and a downstream side along the relative movement direction with respect to the line sensor camera group.

11. The shape inspection method for the metallic body according to claim 9, wherein the first angle and the second angle are each set to 30 degrees or more.

12. The shape inspection method for the metallic body according to claim 9,
wherein the plurality of illumination light sources includes three or more illumination light sources, and
the arithmetic processing apparatus decides beforehand a combination of peak wavelengths of the illumination light that provides the reflected light used in calculating the difference on the basis of a reflection spectrum of the metallic body.

13. The shape inspection method for the metallic body according to claim 9,
wherein the plurality of illumination light sources includes three or more illumination light sources, the illumination light source being arranged in a manner that a longitudinal direction of the illumination light source is substantially parallel to a width direction of the metallic body, and
the arithmetic processing apparatus dynamically decides a combination of peak wavelengths of the illumination light that provides the reflected light used in calculating the difference in a manner that the combination makes an in-plane average value of the calculated differences closest to zero.

14. The shape inspection method for the metallic body according to claim 9, wherein the arithmetic processing apparatus specifies a direction of the inclination on the basis of a sign of the difference and specifies a magnitude of the inclination on the basis of an absolute value of the difference.

15. The shape inspection method for the metallic body according to claim 9, wherein the arithmetic processing apparatus further calculates a height of the surface of the metallic body as the information by integrating the calculated inclination of the surface of the metallic body along the relative movement direction of the monochrome line sensor cameras and the metallic body.

16. The shape inspection method for the metallic body according to claim 9, wherein the arithmetic processing apparatus inspects the shape of the metallic body by comparing the calculated inclination of the surface of the metallic body with a predetermined threshold value.

* * * * *